United States Patent
Guo et al.

(10) Patent No.: US 10,143,720 B2
(45) Date of Patent: Dec. 4, 2018

(54) MODULATION OF HEPATITIS B VIRUS CCCDNA TRANSCRIPTION

(71) Applicants: DREXEL UNIVERSITY, Philadelphia, PA (US); BARUCH S. BLUMBERG INSTITUTE, Doylestown, PA (US)

(72) Inventors: Ju-Tao Guo, Lansdale, PA (US); Jinhong Chang, Chalfont, PA (US); Timothy M. Block, Doylestown, PA (US); William A. Kinney, Newtown, PA (US); Harold R. Almond, Maple Glen, PA (US)

(73) Assignees: Drexel University, Philadelphia, PA (US); Baruch S. Blumberg Institute, Doylestown, PA (US)

( * ) Notice: Subject to any disclaimer, the term of this patent is extended or adjusted under 35 U.S.C. 154(b) by 0 days.

(21) Appl. No.: 15/483,711

(22) Filed: Apr. 10, 2017

(65) Prior Publication Data

US 2017/0296619 A1    Oct. 19, 2017

Related U.S. Application Data

(63) Continuation of application No. 14/435,675, filed as application No. PCT/US2013/043691 on May 31, 2013, now Pat. No. 9,623,071.

(60) Provisional application No. 61/654,374, filed on Jun. 1, 2012.

(51) Int. Cl.
| | |
|---|---|
| *A01N 37/18* | (2006.01) |
| *A61K 38/00* | (2006.01) |
| *A61P 1/16* | (2006.01) |
| *A61K 38/12* | (2006.01) |
| *A61K 31/16* | (2006.01) |
| *A61K 31/165* | (2006.01) |
| *A61K 31/166* | (2006.01) |
| *A61K 45/06* | (2006.01) |
| *C07K 5/12* | (2006.01) |

(52) U.S. Cl.
CPC .............. *A61K 38/12* (2013.01); *A61K 31/16* (2013.01); *A61K 31/165* (2013.01); *A61K 31/166* (2013.01); *A61K 45/06* (2013.01); *C07K 5/123* (2013.01); *C07K 5/126* (2013.01)

(58) Field of Classification Search
CPC .. A61K 31/00; A61K 31/675; A61K 31/7056; C07K 2319/80
USPC ......................................................... 514/4.3
See application file for complete search history.

(56) References Cited

U.S. PATENT DOCUMENTS

| 2004/0014647 A1 | 1/2004 | Lee et al. |
| 2010/0009970 A1 | 1/2010 | Johansen et al. |
| 2011/0245154 A1 | 10/2011 | Berenson et al. |

FOREIGN PATENT DOCUMENTS

| WO | 2011038224 A1 | 3/2011 |
| WO | 2011113013 A2 | 9/2011 |

OTHER PUBLICATIONS

Belloni, L. et al., "IFN-alpha Inhibits HBV Transcription and Replication in Cell Culture and in Humanized Mice by Targeting the Epigenetic Regulation of the Nucelar cccDNA Minichromosome," The Journal of Clinical Investigation, 2012, vol. 122, No. 2, pp. 529-537.
Horne, W.S. et al., "Probing the Bioactive Conformation of an Archetypal Natural Product HDAC Inhibitor Using Conformationally Homogeneous Triazole-Modified Cyclic Tetrapeptides," Angew Chem Int Ed Engl., 2009, vol. 48(26), pp. 4718-4724.
Pollicino, T. et al., "Hepatitis B Virus Replication is Regulated by the Acetylation Status of Hepatitis B Virus cccDNA-Bound H3 and H4 Histones," Gastroenterology, 2006, vol. 130, pp. 823-837.
Ververis, K. et al., "Potential Non-Oncological Applications of Histone Deacetylase Inhibitors," Am. J. Transl. Res., 2011, vol. 3, No. 5, pp. 454-467.
"CAS Registry No. 1126426-52-5", Cyclo[L-alanyl-(2S)-2-amino-8-oxodecanoyl-L-tryptophyl-L-leucyl], 2009.
"CAS Registry No. 1126426-54-7", Cyclo[L-alanyl-(2S)-2-amino-8-oxodecanoyl-D-tryptophyl-L-leucyl], 2009.
"CAS Registry No. 1126426-56-9", Cyclo[L-alanyl-(2S)-2-amino-8-(hydroxyamino)-8-oxooctanoyl-L-tryptophyl-L-leucyl], 2009.
"CAS Registry No. 1126426-59-2", Cyclo[D-alanyl-(2S)-2-amino-8-oxodecanoyl-L-tryptophyl-L-leucyl], 2009.
"CAS Registry No. 1126426-60-5", Cyclo[L-alanyl-(2R)-2-amino-8-oxodecanoyl-L-tryptophyl-L-leucyl], 2009.
"CAS Registry No. 1126426-63-8", Cyclo[N-methyl-L-alanyl-(2S)-2-amino-8-oxodecanoyl-L-tryptophyl-L-leucyl], 2009.
"CAS Registry No. 1187754-56-8", Cyclo-[L-alanyl-(2S)-2-amino-8-oxodecanoyl-L-tryptophyl-(3S)-3-amino-5-methylexanoyl], 2009.
"CAS Registry No. 1187754-57-9", Cyclo[L-alanyl-(2S)-2-amino-8-(hydroxyamino)-8-oxooctanoyl-L-trytophyl-(3S)-3-amino-5-methylhexanoyl], 2009.
"CAS Registry No. 1187754-68-2", Cyclo[(3S)-3-amino-5-methylhexanoyl-N6-acetyl-L-lysyl-(2S)-2-amino-8-oxodecanoyl-L-tryptophyl], 2009.
"CAS Registry No. 1187754-69-3", 1,4,7,10-tetraazacyclotridecane-2,5,8,11-tetrone, 3-(1H-indol-3-ylmethyl)-13-(2-methylpropery1)-6,9-bis(6-oxooctyl)-(3S,6S,9S,13S)-, 2009.

(Continued)

*Primary Examiner* — Hasan Syed Ahmed
*Assistant Examiner* — Kaipeen E Yang
(74) *Attorney, Agent, or Firm* — Saul Ewing Arnstein & Lehr LLP; Kathryn Doyle; Domingos J. Silva

(57) ABSTRACT

The present invention provides small molecule inhibitors of hepatitis B virus (HBV) covalently closed circular (ccc) DNA, which are useful as therapeutics in the management of chronic HBV. The compounds of the invention achieve epigenetic modification of the cccDNA, histone modification and histone deacetylase activity inhibition, thus modulating HBV cccDNA. The present invention further provides methods for modulating HBV cccDNA, for treating or preventing HBV in a subject, and for modulating cccDNA transcription of hepatitis B in a subject.

5 Claims, 2 Drawing Sheets
Specification includes a Sequence Listing.

(56) References Cited

OTHER PUBLICATIONS

"CAS Registry No. 1187754-77-3", Cyclo[(3S)-3-amino-5-methylhexanoyl-L-phenylalanyl-(2S)-2-amino-8-oxodecanoyl-L-tryptophyl], 2009.
"CAS Registry No. 1187754-79-5", Cyclo[(2S)-2-amino-8-(hydroxyamino)-8-oxooctanoyl-L-tryptophyl-(3S)-3-amino-5-methylhexanoyl-L-phenylalanyl], 2009.
"CAS Registry No. 1316753-00-0", 1,4,7,10-tetraazacyclotridecane-2,5,8,11-tetrone,3-(1H-indol-3-ylmethyl)-9,10-dimethyl-13-(2-methylpropyl)-6-(6-oxooctyl)-(3S,6S,9S,13S)-, 2011.
"CAS Registry No. 1316753-02-2", 1,4,7,10-tetraazocyclotridecane-2,5,8,1-tetrone,3-(1H-indol-3-ylmethyl)-9-rnethyl-13-(2-methyl-13-(2-methylpropyl)-6-(6-oxooctyl)-(3S,6S,9R,13S)-, 2011.
"CAS Registry No. 1349396-08-2", Compound according to formula II where R8 is iso-butyl, R1 is CH2, R2 is -C(O)NH-, R3 is (CH2)5NHAc and R6 is (CH2)5C(O)CH2CH3, 2011.
"CAS Registry No. 1373504-57-4", Cyclo[L-alanyl-(2S)-2-aminooctanoyl-L-tryptophyl-(3S)-3-amino-5-methylhexanoyl], 2012.
"CAS Registry No. 1373504-63-2", Cyclo[L-alanyl-L-norleucyl-L-tryptophyl-(3)-3-amino-5-methylhexanoyl], 2012.
"CAS Registry No. 1373504-64-3", Cyclo[L-alanyl-L-norvalyl-L-tryptophyl-(3S)-3-amino-5-methylhexanoyl], 2012.
"CAS Registry No. 1373504-65-4", Cyclo[(3S)-3-amino-5-methylhexanoyl-3-methoxy-L-phenylalanyl-L-norvalyl-L-tryptophyl], 2012.
"CAS Registry No. 1373504-66-5", Cyclo[(3S)-3-amino-5-methylhexanoyl-L-phenylalanyl-L-norvalyl-L-tryptophyl], 2012.
"CAS Registry No. 1373504-68-7", Cyclo[(3S)-3-amino-5-methylhexanoyl-L-phenylalanyl-L-norvalyl-L-tryptophyl], 2012.
"CAS Registry No. 1373504-69-8", Cyclo[3-(3-pyridinyl)-L-alanyl-L-norvalyl-L-tryptophyl-(3S)-3-amino-5-methylhexanoyl], 2012.
"CAS Registry No. 1373504-70-1", Cyclo[(3S)-3-amino-5-methylhexanoyl-L-leucyl-L-norvalyl-L-tryptophyl], 2012.
"CAS Registry No. 1373504-71-2", Cyclo[D-alanyl-L-norvalyl-L-tryptophyl-(3S)-3-amino-5-methylhexanoyl], 2012.
"CAS Registry No. 1373504-72-3", Cyclo[(2S)-2-aminobutanoyl-L-norvalyl-L-tryptophyl-(3S)-3-amino-5-methylhexanoyl], 2012.
"CAS Registry No. 1373504-73-4", Cyclo[(3S)-3-amino-5-methylhexanoylglycyl-L-norvalyl-L-tryptophyl], 2012.
"CAS Registry No. 1373504-74-5", Cyclo[(3S)-3-amino-5-methylhexanoyl-L-asparaginyl-L-norvalyl-L-tryptophyl], 2012.
Cai, et al., "Identification of Disubstituted Sulfonamide Compounds as Specific Inhibitors of Hepatitis B Virus Covalently Closed Circular DNA Formation", Antimicrobial Agents and Chemotherapy, vol. 56, No. 8, 2012, pp. 4277-4288.
Hutt, et al., "Potential Agents for Treating Cystic Fibrosis: Cyclic Tetrapeptides that Restore Trafficking and Activity of F508-CFTR", ACS Med Chem Lett, vol. 2, No. 9, 2011, pp. 703-707.
Vickers, et al., "Discovery of HDAC Inhibitors that Lack an Active Site Zn2+-Binding Functional Group", ACS Med Chem Lett, vol. 3, No. 6, 2012, pp. 505-508.
Balasubramanian, et al., "Isoform-Specific Histone Deacetylase Inhibitors: The Next Step?", Cancer Letters, vol. 280, 2009, pp. 211-221.
Olsen, et al., "Discovery of Potent and Selective Histone Deacetylase Inhibitors via Focused Combinatorial Libraries of Cyclic alpha3beta-Tetrapeptides", J. Med. Chem., vol. 52, 2009, pp. 7836-7846.

SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Chemically synthesized

<400> SEQUENCE: 1

```
gatccccgca ga                                                12

<210> SEQ ID NO 2
<211> LENGTH: 16
<212> TYPE: DNA
<213> ORGANISM: Artificial Sequence
<220> FEATURE:
<223> OTHER INFORMATION: Chemically synthesized

<400> SEQUENCE: 2
atctgctttt tggaaa                                            16
```

MODULATION OF HEPATITIS B VIRUS CCCDNA TRANSCRIPTION

CROSS-REFERENCE TO RELATED APPLICATIONS

This application is a continuation of, and claims priority to, U.S. patent application Ser. No. 14/435,675, filed Apr. 14, 2015, now issued as U.S. Pat. No. 9,623,071, which is the U.S. National Phase Application filed under 35 U.S.C. § 371 claiming priority to PCT International Application No. PCT/US2013/043691, filed May 31, 2013, which claims priority to U.S. Provisional Application No. 61/654,374, filed Jun. 1, 2012, all of which applications are hereby incorporated herein by reference in their entireties.

TECHNICAL FIELD

The present disclosure pertains to the use of pharmacological agents, preferably with histone deacetylase activity, for modulating covalently closed circular DNA of hepatitis B virus, and for preventing or treating hepatitis B.

BACKGROUND

There are now seven medications approved by the United States Food & Drug Administration (FDA) for the management of chronic hepatitis B, which fall into one of two categories: the interferons (IFNs) and the polymerase inhibitors (Lok, A. S., and B. J. McMahon. 2007. *Chronic Hepatitis B. Hepatology* 45:507-539). These are recommended for use in approximately 50% or less of the infected population of more than 350 million. Although this is the highest risk population, those who fall outside the treatment guidelines may also benefit from intervention, since they are also at significantly elevated risk of liver diseases. The IFNs are limited by significant side effects. The pol inhibitors target the same viral life cycle step and thus combination therapy, the bulwark of HIV and curative HCV therapy, is of limited value. They require lifelong use, and are subject to eventual use limiting toxicities, as seen with HIV long term medication use, and the emergence of drug resistant mutants. Thus, alternatives and complements to the current portfolio of medications are needed.

There is a growing belief that a "cure", or at least sustained off-drug control of HBV, will require, or at least benefit from, drugs that control the viral nuclear genome, the covalently closed circular DNA (cccDNA). The 2006 NIDDK Liver Action Plan, reinforced by the 2010 Institute of Medicine report, all call for cccDNA inhibition as a priority for HBV drug development.

However, screening for HBV cccDNA inhibitors has been difficult, because of technical reasons: HBV cccDNA is made in amounts to low to be conveniently detected, and most viral gene products in conventionally transfected cells in culture are derived from transgenes of the viral genome, not cccDNA. The present inventors have created cell lines in which HBV gene products such as the HBeAg are produced only from cccDNA, but not from integrated viral transgene and in amounts to be robustly detected, making screening realistic (Cai, D., et al., 2012. *Identification of the Disubstituted Sulfonamide Compounds as Specific Inhibitors of Hepatitis B Virus Covalently Closed Circular DNA Formation. Antimicrobial Agents and Chemotherapy: In Press*; Zhou, T, et al., 2006. *Hepatitis B virus e antigen production is dependent upon covalently closed circular (ccc) DNA in HepAD38 cell cultures and may serve as a cccDNA surrogate in antiviral screening assays. Antiviral Research* 72:116-124).

Given such challenges, it is unsurprising that there are no HBV therapeutics in use that target HBV cccDNA and, there have been few, if any, programs to screen and develop cccDNA inhibitors. This is largely due to technical difficulties (see Block, T M, et al. 2003. *Molecular viral oncology of hepatocellular carcinoma. Oncogene* 22:5093-5107; Locarnini, S. 2005. *Therapies for hepatitis B: where to from here? Gastroenterology* 128: 789-792; Lok, A. S. 2011. *Does antiviral therapy for hepatitis B and C prevent hepatocellular carcinoma? J Gastroenterol Hepatol* 26:221-227). In addition, the role of host functions in regulating HBV cccDNA transcription and stability is poorly understood further frustrating development of therapeutics. Thus, any work in this area would be innovative, and would address the outstanding and long-felt need for drugs that control the viral nuclear genome of hepatitis B and otherwise provide treatment for HBV infection.

SUMMARY

Provided are methods of modulating cccDNA transcription of hepatitis B in a subject comprising administering to the subject an agent that provides epigenetic modification of the cccDNA, a histone modifying agent, or an inhibitor of histone deacetylase activity. For example, the epigenetic modifying agent, histone modifying agent, or inhibitor of histone deacetylase activity may be pharmacological, such as a small molecule.

Also provided are methods of treating hepatitis B in a subject comprising administering to the subject an inhibitor of histone deacetylase activity.

The present disclosure also pertains to method of modulating hepatitis B virus covalently closed circular DNA comprising contacting a hepatitis B virus with an inhibitor of histone deacetylase activity.

Also disclosed are compounds according to formula II:

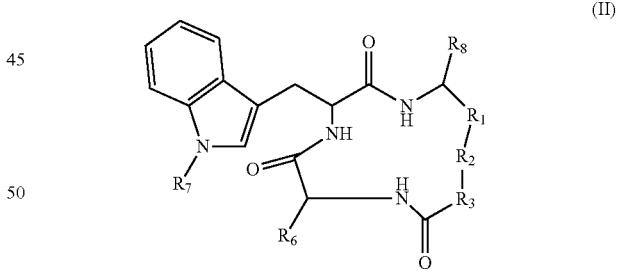

wherein $R_1$-$R_8$ are defined as provided herein.

DETAILED DESCRIPTION OF ILLUSTRATIVE EMBODIMENTS

Figure 1:
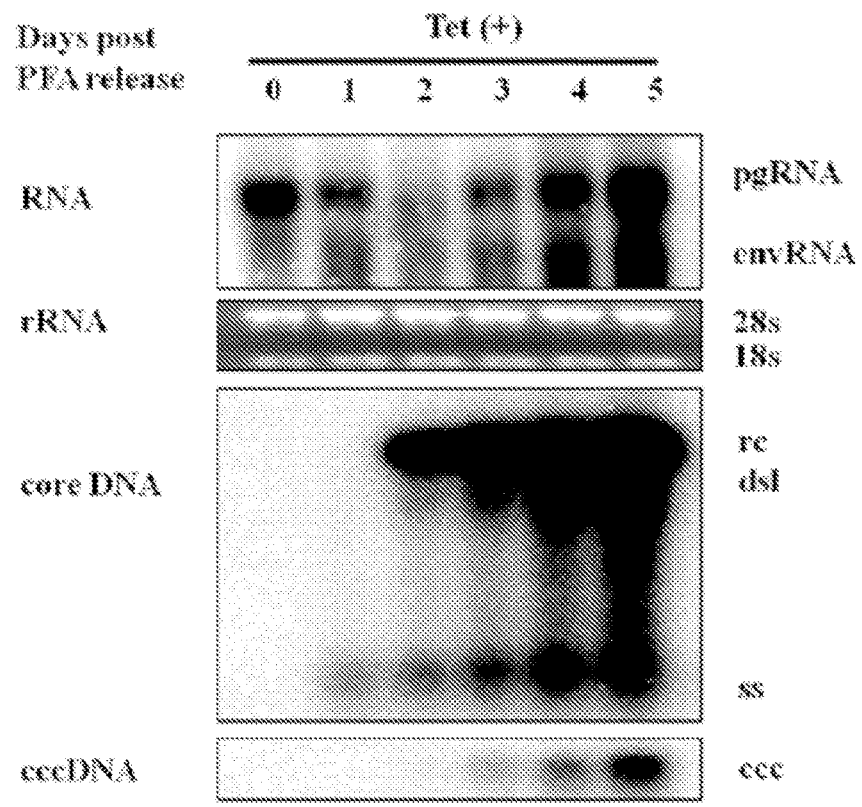
FIG. 1 provides data demonstrating that HBV cccDNA is efficiently formed and transcriptionally active in dstet5 cells.

The present invention may be understood more readily by reference to the following detailed description taken in connection with the accompanying figures and examples, which form a part this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The disclosures of each patent, patent application, and publication cited or described in this document are hereby incorporated herein by reference, in their entirety.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. Furthermore, when indicating that a certain chemical moiety "may be" X, Y, or Z, it is not intended by such usage to exclude in all instances other choices for the moiety; for example, a statement to the effect that $R_1$ "may be alkyl, aryl, or amino" does not necessarily exclude other choices for $R_1$, such as halo, aralkyl, and the like.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." In another example, when a listing of possible substituents including "hydrogen, alkyl, and aryl" or ""hydrogen, alkyl, or aryl" is provided, the recited listing may be construed as including situations whereby any of "hydrogen, alkyl, and aryl" or "hydrogen, alkyl, or aryl" is negatively excluded; thus, a recitation of "hydrogen, alkyl, and aryl" or "hydrogen, alkyl, and aryl" may be construed as "hydrogen and/or aryl, but not alkyl", or simply "wherein the substituent is not alkyl".

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "µg" means microgram(s), "eq" means equivalent(s), "h" means hour(s), "µL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

"Apicidin" is a compound derived from a *Fusarium* species fungal metabolite. It has the structure cyclo(N—O-methyl-L-tryptophanyl-L-isoleucinyl-D-pipecolinyl-L-2-amino-8-oxodecanoyl).

"Natural analogs of Apicidin" refers to analogs of Apicidin that are produced in fermentations of *Fusarium pallidoroseum* species ATCC74322 and ATCC47289 (Apicidins A, B, C, D1, D2, D3, which are described in *JOC* 67, 815 (2002) and *Tet Lett,* 37, 8077 (1996), and in WO 1996/9603428.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Where appropriate, "alkyl" can mean "alkylene"; for example, if X is and $R_1$ is said to be "alkyl", then "alkyl" may correctly be interpreted to mean "alkylene".

"Amino" refers to —$NH_2$ and may include one or more substituents that replace hydrogen. "Amino" is used interchangeably with amine and is also intended to include any pharmaceutically acceptable amine salts. For example, amino may refer to —$NH^+(X)(Y)Cl^-$, wherein X and Y are preferably and independently hydrogen or alkyl, wherein alkyl may include one or more halo substitutions.

As used herein, "aryl", "arene", and "aromatic" each refer to an optionally substituted, saturated or unsaturated, monocyclic, polycyclic, or other homo-, carbo- or heterocyclic aromatic ring system having from about 3 to about 50 ring members (and all combinations and subcombinations of ranges and specific numbers of carbon atoms therein), with from about 5 to about 10 ring atom members being preferred. Such moieties encompass (include) "heteroaryl" and "heteroarene" as defined infra. Where appropriate, "aryl" can mean "arene"; for example, if X is —$R_1R_2$, and $R_1$ is said to be "aryl", then "aryl" may correctly be interpreted to mean "arene".

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

As used herein, "aralkyl" refers to alkyl radicals bearing one or more aryl substituents and having from about 4 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms.

In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkylamido" refers to alkyl-CH(=O)NH—, wherein alkyl is as previously described. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-SO$_2$—, wherein alkyl is as previously defined. "Aminooxy" as used herein refers to the group amino-(O)—, wherein amino is defined as above. "Aralkylaminooxy" as used herein is used to denote aryl-akyl-aminooxy-, wherein aryl, alkyl, and aminooxy are respectively defined as provided previously.

As used herein, "alkylene" refers to an optionally branched or substituted bivalent alkyl radical having the general formula —(CH$_2$)$_n$—, where n is 1 to 10. Non-limiting examples include methylene, trimethylene, pentamethylene, and hexamethylene.

"Alkyleneamino" refers to —(CH$_2$)$_n$—NH—, where n is 1 to 10 and wherein the bivalent alkyl radical may be optionally branched or substituted, and the amino group may include one or more substituents that replace hydrogen.

As used herein, "heteroaryl" or "heteroarene" refers to an aryl radical wherein in at least one of the rings, one or more of the carbon atom ring members is independently replaced by a heteroatom group selected from the group consisting of S, O, N, and NH, wherein aryl is as previously defined. Heteroaryl/heteroarene groups having a total of from about 3 to about 14 carbon atom ring members and heteroatom ring members are preferred. Likewise, a "heterocyclic ring" is an aryl radical wherein one or more of the carbon atom ring members may be (but are not necessarily) independently replaced by a heteroatom group selected from the group consisting of S, O, N, and NH. Heterocyclic rings having a total from about 3 to 14 ring members and heteroatom ring members are preferred, but not necessarily present; for example, "heterocyclohexyl" may be a six-membered aryl radical with or without a heteroatom group.

"Halo" and "halogen" each refers to a fluoro, chloro, bromo, or iodo moiety, with fluoro, chloro, or bromo being preferred.

"Haloalkyl" signifies halo-alkyl- wherein alkyl and halo, respectively, are as previously described.

The phrase reading "[moiety] is absent" may mean that the substituents to which the moiety is attached are directly attached to each other.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), oxo (=O), carboxy (—COOH), —O—C(=O)R", —C(=O)R", —OR", —C(=O)OR", -(alkylene)-C(=O)—OR", —NHC(=O)R", aminocarbonyl (—C(=O)NH$_2$), —N-substituted aminocarbonyl (—C(=O)NHR"), —N,N-disubstituted aminocarbonyl (—C(=O)N(R")R"), thiol, thiolato (—SR"), sulfonic acid (—SO$_3$H), phosphonic acid (—PO$_3$H), —P(=O)(OR")OR", —S(=O)R", —S(=O)$_2$R", —S(=O)$_2$NH$_2$, —S(=O)$_2$ NHR", —S(=O)$_2$NR"R", —NHS(=O)$_2$R", —NR"S(=O)$_2$R", —CF$_3$, —CF$_2$CF$_3$, —NHC(=O)NHR", —NHC(=O)NR"R", —NR"C(=O) NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer>1) including, for example, dihydrates ($R.2H_2O$), trihydrates ($R.3H_2O$), and the like, or hemihydrates, such as, for example, $R.n_{1/2}H_2O$, $R.n_{1/3}H_2O$, $R.n_{1/4}H_2O$ and the like wherein n is an integer.

"Solvate" refers to a compound of the present invention which is associated with solvent in the molecular form, i.e., in which the solvent is coordinatively bound, and may be represented, for example, by the formula R-(solvent), where R is a compound of the invention. A given compound may form more than one solvate including, for example, mono-solvates (R.(solvent)) or polysolvates (R.n(solvent)) wherein n is an integer>1) including, for example, disolvates (R.2(solvent)), trisolvates (R.3(solvent)), and the like, or hemisolvates, such as, for example, $R.n_{1/2}$(solvent), $R.n_{1/3}$(solvent), $R.n_{1/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

An "isotopically substituted analogue" is a compound of the present disclosure in which one or more atoms have been replaced with an isotope of that atom. For example, hydrogen (protium) may be substituted with deuterium or tritium. Other atoms that may be replaced with an isotope thereof in order to form an isotopically substituted analogue thereof include, for example, carbon (replaced with $C^{13}$), nitrogen (replaced with $N^{15}$), iodine (replaced with $I^{131}$), fluorine (replaced with $F^{18}$), or sulfur (replaced with $S^{31}$). Any available isotope may be used to form an isotopically substituted analogue thereof, and those of ordinary skill in the art will recognize available techniques for forming such analogues from a given compound.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

"Subject" or "patient" refers to an embryonic, immature, or adult animal, including the human species, that is treatable with the compositions, and/or methods of the present invention.

It has presently been discovered that hepatitis B virus covalently closed circular DNA (cccDNA), existing and being expressed as an "episome" in the nucleus of an infected cell, is regulated differently than HBV DNA integrated in to the host chromosome, and that RNA expression from the HBV cccDNA can be pharmacologically suppressed, selectively, as compared to other genes (as described more fully herein). Indeed, the present inventors have identified numerous compounds that repress DHBV cccDNA transcription in a reproducible and robust manner, and that occurs at low concentrations and under conditions of no apparent toxicity. These results represent the first time that selective pharmacological suppression has been achieved, by design, with small molecules. The result that gene expression from HBV cccDNA is regulated differently that the same or similar DNA integrated in to the host chromosomes is surprising and a highly useful observation, in that it enables therapies that selectively repress cccDNA DNA (for example, as compared with integrated HBV DNA) without suppressing or otherwise affecting host chromosomal DNA. The present finding that HBV cccDNA can be suppressed pharmacologically was heretofore unknown, and offers the proof of useful concept of the prior statement, and demonstrates that such pharmacological suppression is possible.

Accordingly, the present disclosure provides, inter alia, methods of modulating cccDNA transcription of hepatitis B in a subject comprising administering to the subject an agent that provides epigenetic modification of the cccDNA, a histone modifying agent, or an inhibitor of histone deacetylase activity. For example, the epigenetic modifying agent, histone modifying agent, or inhibitor of histone deacetylase activity may be pharmacological, such as a small molecule. The epigenetic modifying agent, histone modifying agent, or inhibitor of histone deacetylase activity may be selective for the inhibition of cccDNA, as compared with integrated HBV DNA, i.e., does not inhibit integrated HBV DNA, and/or as compared with cellular host DNA, i.e., does not inhibit cellular host DNA. The inhibitor of histone deacetylase activity may be an inhibitor of multiple classes of histone deacetylase, or may be selective for a particular class of histone deacetylase. For example, the inhibitor may be an inhibitor of class I histone deacetylase activity, class II histone deacetylase activity, or both. Preferably, the inhibitor of histone deacetylase activity is an inhibitor of class I histone deacetylase activity. Numerous inhibitors of histone deacetylase activity are known, and any such HDAC inhibitor may be used pursuant to the present methods.

The present methods of modulating cccDNA transcription of hepatitis B may also include—in addition to the administration to the subject an agent that provides epigenetic modification of the cccDNA, a histone modifying agent, or an inhibitor of histone deacetylase activity—administering to the subject a therapeutically effective amount of a further agent that modulates hepatitis B virus. The further agent may be administered simultaneously with, or simply as a part of the same general therapy regimen as the agent that provides epigenetic modification of the cccDNA, histone modifying agent, or inhibitor of histone deacetylase activity. The further agent may be any substance that is presently used for modulation of HBV, of which numerous types are known among those skill in the art. For example, existing drugs for the modulation of HBV include interferons (e.g., interferon alpha, pegylated interferon), nucleoside analogues (e.g., lamivudine, adefovir dipivoxil, entecavir, telbivudine, tenofovir, clevudine, amdoxovir), non-nucleoside antivirals (e.g., BAM 205, ANA380, myrcludex B, HAP Compound Bay 41-4109, REP 9AC, nitazoxanide, dd-RNAi compound, ARC-520, NVR-1221), non-interferon immune enhancers (e.g., thymosin alpha-1, interleukin-7, DV-601, HBV core antigen vaccine, GS-9620, GI13000), and post-exposure and/or post-liver transplant treatment drugs (e.g., hyperHEP S/D, Nabi-GB, Hepa Gam B).

In particular, the further agent may be any other Direct Acting Antiviral anti hepatitis B agent (such as the polymerase inhibitors Barraclude, Tenofovir, lamivudine, telbivudine, and adefovir) and/or any other directing acting antiviral agents that work at a step in the virus life cycle other than suppression of cccDNA transcription, such as capsid inhibitors, secretion inhibitors, or entry inhibitors. The further agent may also be any other non-direct acting antiviral agent, such as an interferon or other immunomodulatory agent.

In accordance with the present methods of modulating cccDNA transcription of hepatitis B, the inhibitor of histone deacetylase activity may be, for example, Trichostatin A, suberoyl bis hydroxamic acid, 4-(dimethylamino)-N-[7-(hydroxyamino)-7-oxoheptyl] benzamide, Apicidin, an Apicidin analog (for example, a natural analog of Apicidin or an analog that is synthesized de novo), or a compound according to formula (I)

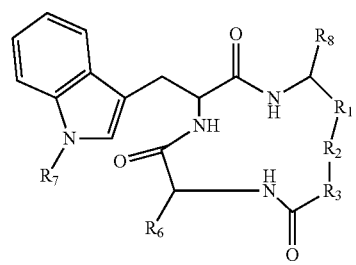

(I)

wherein $R_1$ is —$(CH_2)_n$— or —C(=O)—;

$R_2$ is —C(=O)—, 3,5-triazolyl, or —C(Z)N($R_4$)—;

$R_4$ is hydrogen, alkyl, aryl, aralkyl, dialkylaminoalkyl, or carboxyalkyl;

$R_3$ is —CH($R_5$)—, or $R_2$ is nitrogen and $R_3$ is —CH— and $R_2$ and $R_3$ together form piperidinyl;

$R_5$ is hydrogen, —$CH_3$, or an alpha amino acid R group;

$R_6$ is —$(CH_2)_m$C(X)Y, —$(CH_2)_2CH_3$, or —$(CH_2)_q$-phenyl-$(CH_2)_m$C(=O)NHOH;

X is =O, $H_2$, =N—$NH_2$, or =N—NH—C(=O)$NH_2$;

Y is NHOH or —$CH_2CH_3$;

Z is $H_2$ or O;

$R_7$ is hydrogen or alkoxy;

$R_8$ is alkyl or carboxyalkyl;

n is 0-2;

m is 0-6; and, q is 0-3;

or a stereoisomer or pharmaceutically acceptable salt thereof.

As used herein, the phrase "alpha amino acid R group" refers to a side chain group from a natural or unnatural amino acid.

In certain embodiments, the inhibitor of histone deacetylase activity is Apicidin,

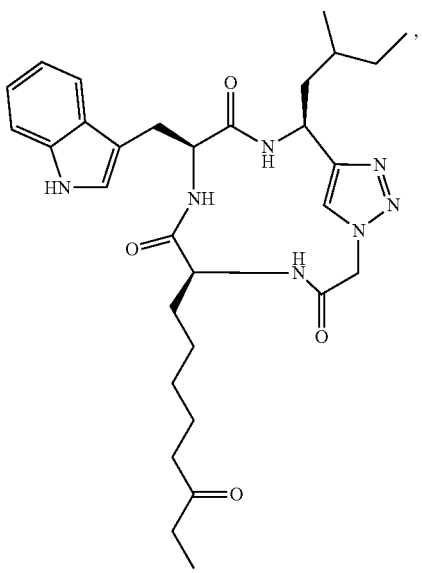

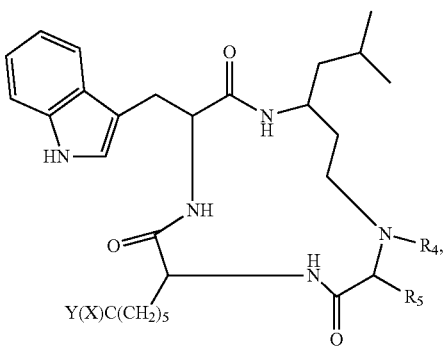

or a stereoisomer or pharmaceutically acceptable salt thereof.

The present disclosure also pertains to methods of treating hepatitis B in a subject comprising administering to the subject an agent that provides epigenetic modification of the cccDNA, a histone modifying agent, or an inhibitor of histone deacetylase activity. For example, the epigenetic modifying agent, histone modifying agent, or inhibitor of histone deacetylase activity may be pharmacological, such as a small molecule. The epigenetic modifying agent, histone modifying agent, or inhibitor of histone deacetylase activity may be selective for the inhibition of cccDNA, as compared with integrated HBV DNA, i.e., does not inhibit integrated HBV DNA, and/or as compared with cellular host DNA, i.e., does not inhibit cellular host DNA. The inhibitor of histone deacetylase activity may be an inhibitor of multiple classes of histone deacetylase, or may be selective for a particular class of histone deacetylase. For example, the inhibitor may be an inhibitor of class I histone deacetylase activity, class II histone deacetylase activity, or both. Preferably, the inhibitor of histone deacetylase activity is an inhibitor of class I histone deacetylase activity. Numerous inhibitors of histone deacetylase activity are known, and any such HDAC inhibitor may be used pursuant to the present methods.

In accordance with the present methods of treating hepatitis B in a subject, the inhibitor of histone deacetylase activity may be, for example, Trichostatin A, suberoyl bis hydroxamic acid, 4-(dimethylamino)-N-[7-(hydroxyamino)-7-oxoheptyl]benzamide, Apicidin, an Apicidin analog (for example, a natural analog of Apicidin or an analog that is synthesized de novo), or a compound according to formula (I)

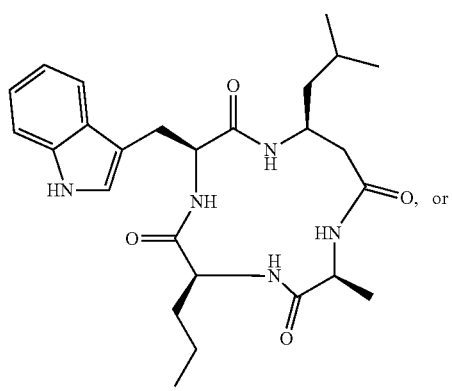

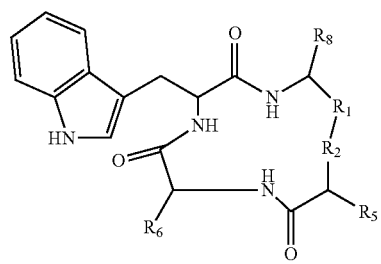

wherein
$R_1$ is —(CH$_2$)—,
and,
$R_2$ is —C(Z)N(R$_4$)—
or a stereoisomer or pharmaceutically acceptable salt thereof.

In other embodiments, the inhibitor of histone deacetylase activity is (I)

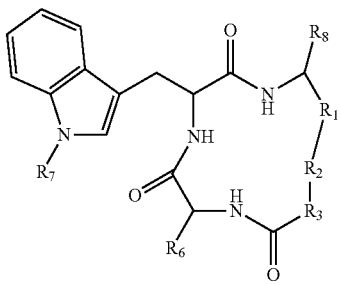

wherein
$R_1$ is —(CH$_2$)$_n$— or —C(=O)—;
$R_2$ is —C(=O)—, 3,5-triazolyl, or —C(Z)N(R$_4$)—;

$R_4$ is hydrogen, alkyl, aryl, aralkyl, dialkylaminoalkyl, or carboxyalkyl;

$R_3$ is —CH($R_5$)—, or $R_2$ is nitrogen and $R_3$ is —CH— and $R_2$ and $R_3$ together form piperidinyl;

$R_5$ is hydrogen, —CH$_3$, or an alpha amino acid R group;

$R_6$ is —(CH$_2$)$_m$C(X)Y, —(CH$_2$)$_2$CH$_3$, or —(CH$_2$)$_q$-phenyl-(CH$_2$)$_m$C(=O)NHOH;

X is =O, H$_2$, =N—NH$_2$, or =N—NH—C(=O)NH$_2$;

Y is NHOH or —CH$_2$CH$_3$;

Z is H$_2$ or O;

$R_7$ is hydrogen or alkoxy;

$R_8$ is alkyl or carboxyalkyl;

n is 0-2;

m is 0-6; and, q is 0-3;

or a stereoisomer or pharmaceutically acceptable salt thereof.

In certain embodiments, the inhibitor of histone deacetylase activity is Apicidin,

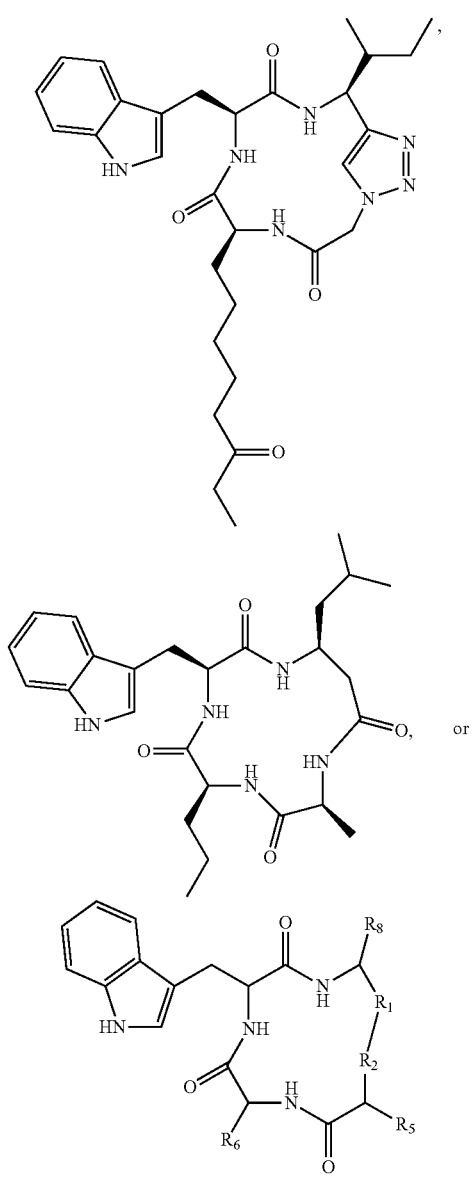

wherein
$R_1$ is —(CH$_2$)—,
and,
$R_2$ is —C(Z)N($R_4$)— or a stereoisomer or pharmaceutically acceptable salt thereof.

In other embodiments, the inhibitor of histone deacetylase activity is

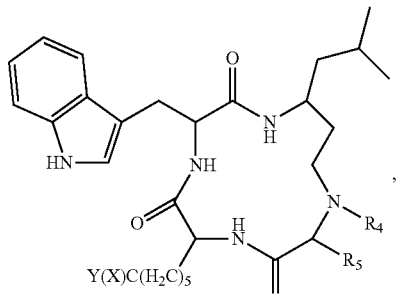

or a stereoisomer or pharmaceutically acceptable salt thereof.

The present methods of treating hepatitis B in a subject may also include—in addition to the administration to the subject an agent that provides epigenetic modification of the cccDNA, a histone modifying agent, or an inhibitor of histone deacetylase activity—administering to the subject a therapeutically effective amount of a further agent that modulates hepatitis B virus. The further agent may be administered simultaneously with, or simply as a part of the same general therapy regimen as the agent that provides epigenetic modification of the cccDNA, histone modifying agent, or inhibitor of histone deacetylase activity. The further agent may be any substance that is presently used for modulation of HBV, of which numerous types are known among those skill in the art. For example, existing drugs for the modulation of HBV include interferons (e.g., interferon alpha, pegylated interferon), nucleoside analogues (e.g., lamivudine, adefovir dipivoxil, entecavir, telbivudine, tenofovir, clevudine, amdoxovir), non-nucleoside antivirals (e.g., BAM 205, ANA380, myrcludex B, HAP Compound Bay 41-4109, REP 9AC, nitazoxanide, dd-RNAi compound, ARC-520, NVR-1221), non-interferon immune enhancers (e.g., thymosin alpha-1, interleukin-7, DV-601, HBV core antigen vaccine, GS-9620, GI13000), and post-exposure and/or post-liver transplant treatment drugs (e.g., hyperHEP S/D, Nabi-GB, Hepa Gam B).

In particular, the further agent may be any other Direct Acting Antiviral anti hepatitis B agent (such as the polymerase inhibitors Barraclude, Tenofovir, lamivudine, telbivudine, and adefovir) and/or any other directing acting antiviral agents that work at a step in the virus life cycle other than suppression of cccDNA transcription, such as capsid inhibitors, secretion inhibitors, or entry inhibitors. The further agent may also be any other non-direct acting antiviral agent, such as an interferon or other immunomodulatory agent.

Also disclosed are methods of modulating hepatitis B virus covalently closed circular DNA comprising contacting a hepatitis B virus with an agent that provides epigenetic modification of the cccDNA, a histone modifying agent, or an inhibitor of histone deacetylase activity. For example, the epigenetic modifying agent, histone modifying agent, or inhibitor of histone deacetylase activity may be pharmacological, such as a small molecule. The epigenetic modifying agent, histone modifying agent, or inhibitor of histone deacetylase activity may be selective for the inhibition of cccDNA, as compared with integrated HBV DNA, i.e., does not inhibit integrated HBV DNA, and/or as compared with cellular host DNA, i.e., does not inhibit cellular host DNA. The inhibitor of histone deacetylase activity may be an inhibitor of multiple classes of histone deacetylase, or may be selective for a particular class of histone deacetylase. For example, the inhibitor may be an inhibitor of class I histone deacetylase activity, class II histone deacetylase activity, or both. Preferably, the inhibitor of histone deacetylase activity is an inhibitor of class I histone deacetylase activity. Numerous inhibitors of histone deacetylase activity are known, and any such HDAC inhibitor may be used pursuant to the present methods.

In accordance with the present methods of modulating hepatitis B virus covalently closed circular DNA, the inhibitor of histone deacetylase activity may be, for example, Trichostatin A, suberoyl bis hydroxamic acid, 4-(dimethylamino)-N-[7-(hydroxyamino)-7-oxoheptyl] benzamide, Apicidin, an Apicidin analog (for example, a natural analog of Apicidin or an analog that is synthesized de novo), or a compound according to formula (I)

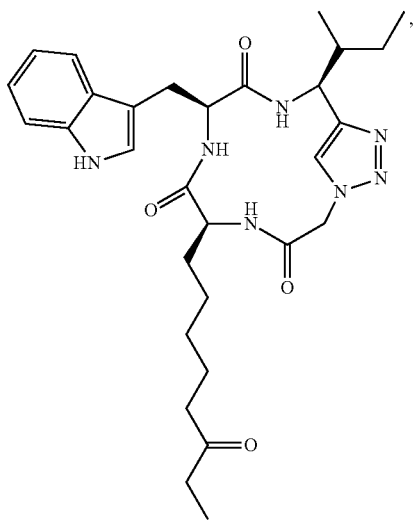

(I)

wherein $R_1$ is —$(CH_2)_n$— or —C(=O)—;

$R_2$ is —C(=O)—, 3,5-triazolyl, or —C(Z)N($R_4$)—;

$R_4$ is hydrogen, alkyl, aryl, aralkyl, dialkylaminoalkyl, or carboxyalkyl;

$R_3$ is —CH($R_5$)—, or $R_2$ is nitrogen and $R_3$ is —CH— and $R_2$ and $R_3$ together form piperidinyl;

$R_5$ is hydrogen, —$CH_3$, or an alpha amino acid R group;

$R_6$ is —$(CH_2)_m$C(X)Y, —$(CH_2)_2CH_3$, or —$(CH_2)_q$-phenyl-$(CH_2)_m$C(=O)NHOH;

X is =O, $H_2$, =N—$NH_2$, or =N—NH—C(=O)$NH_2$;

Y is NHOH or —$CH_2CH_3$;

Z is $H_2$ or O;

$R_7$ is hydrogen or alkoxy;

$R_8$ is alkyl or carboxyalkyl;

n is 0-2;

m is 0-6; and, q is 0-3;

or a stereoisomer or pharmaceutically acceptable salt thereof.

In certain embodiments, the inhibitor of histone deacetylase activity is Apicidin,

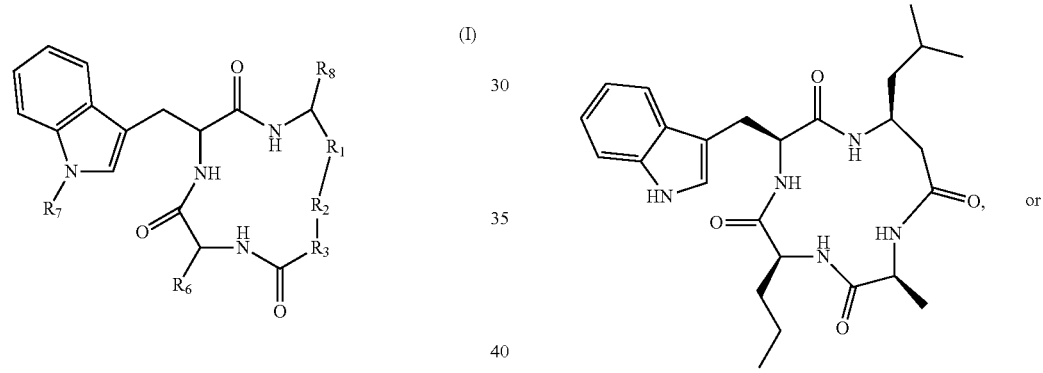

wherein $R_1$ is —$(CH_2)$—, and, $R_2$ is —C(Z)N($R_4$)— or a stereoisomer or pharmaceutically acceptable salt thereof.

In other embodiments, the inhibitor of histone deacetylase activity is

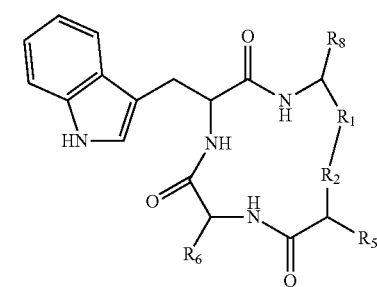

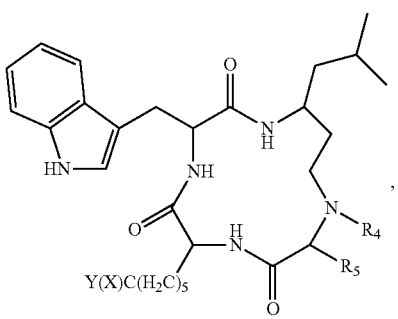

or a stereoisomer or pharmaceutically acceptable salt thereof.

The present methods of modulating hepatitis B virus covalently closed circular DNA may also include—in addition to the contacting of a hepatitis B virus with an agent that provides epigenetic modification of the cccDNA, a histone modifying agent, or an inhibitor of histone deacetylase activity—contacting the hepatitis B virus with a therapeutically effective amount of a further agent that modulates hepatitis B virus. The contacting of the further agent with the HBV may occur simultaneously with, or simply as a part of the same procedure that involves contacting the HBV with the agent that provides epigenetic modification of the cccDNA, histone modifying agent, or inhibitor of histone deacetylase activity. The further agent may be any substance that is presently used for modulation of HBV, of which numerous types are known among those skill in the art. For example, existing drugs for the modulation of HBV include interferons (e.g., interferon alpha, pegylated interferon), nucleoside analogues (e.g., lamivudine, adefovir dipivoxil, entecavir, telbivudine, tenofovir, clevudine, amdoxovir), non-nucleoside antivirals (e.g., BAM 205, ANA380, myrcludex B, HAP Compound Bay 41-4109, REP 9AC, nitazoxanide, dd-RNAi compound, ARC-520, NVR-1221), non-interferon immune enhancers (e.g., thymosin alpha-1, interleukin-7, DV-601, HBV core antigen vaccine, GS-9620, GI13000), and post-exposure and/or post-liver transplant treatment drugs (e.g., hyperHEP S/D, Nabi-GB, Hepa Gam B).

In particular, the further agent may be any other Direct Acting Antiviral anti hepatitis B agent (such as the polymerase inhibitors Barraclude, Tenofovir, lamivudine, telbivudine, and adefovir) and/or any other directing acting antiviral agents that work at a step in the virus life cycle other than suppression of cccDNA transcription, such as capsid inhibitors, secretion inhibitors, or entry inhibitors. The further agent may also be any other non-direct acting antiviral agent, such as an interferon or other immunomodulatory agent.

The present disclosure also pertains to compound according to formula II:

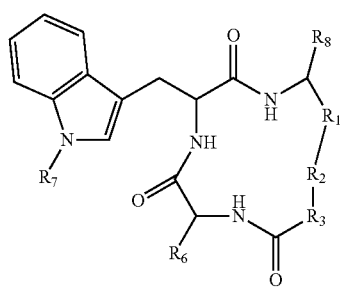

(II)

wherein
$R_1$ is $—(CH_2)_n—$ or $—C(=O)—$;
$R_2$ is $—C(=O)—$ or $—C(Z)N(R_4)—$;
$R_4$ is hydrogen, alkyl, aryl, aralkyl, dialkylaminoalkyl, or carboxyalkyl;
$R_3$ is $—CH(R_5)—$;
$R_5$ is hydrogen, $—CH_3$, or an alpha amino acid R group;
$R_6$ is $—(CH_2)_mC(X)Y$, $—(CH_2)_2CH_3$, or $—(CH_2)_q$-phenyl-$(CH_2)_mC(=O)NHOH$;
X is $=O$, $H_2$, $=N—NH_2$, or $=N—NH—C(=O)NH_2$;
Y is NHOH or $—CH_2CH_3$;
Z is $H_2$ or O;
$R_7$ is hydrogen or alkoxy;
$R_8$ is alkyl or carboxyalkyl;
n is 0-2;
m is 0-6; and,
q is 0-3;
or a stereoisomer or pharmaceutically acceptable salt thereof, For example, the compound may be

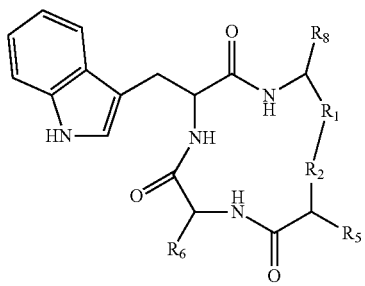

wherein
$R_1$ is $—(CH_2)—$,
and,
$R_2$ is $—C(Z)N(R_4)—$.
In other embodiments, the compound may be

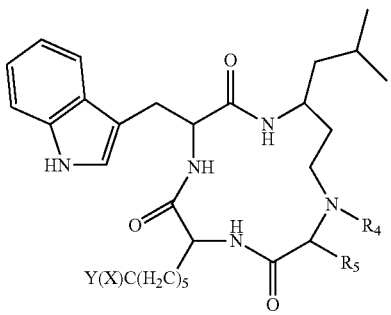

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality in room temperature chemical reaction conditions to which the compound is exposed. Any of a variety of protecting groups may be employed with the present invention. Protecting groups that may be employed in accordance with the present invention may be described in Greene, T W. and Wuts, P. G. M., *Protective Groups in Organic Synthesis* 2d. Ed., Wiley & Sons, 1991.

In a further aspect, the present disclosure relates to pharmaceutical compositions comprising a compound according to formula (I) or (II), or a pharmaceutically acceptable salt, isotopically substituted analogue, or stereoisomer thereof and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety. The pharmaceutical compositions may further comprise a therapeutically effective amount of a further agent that modulates hepatitis B virus. For example, the further agent that modulates virus may be a known anti-viral agents. In certain embodiments, the present compositions comprise a therapeutically effective amount of a compound according to formula (I) or (II) which is administered in combination with immunizations or vaccines that are effective in preventing or lessening the symptoms of HBV. Examples include antibodies, immune suppressants, anti-inflammatory agents, and the like.

As used herein, the term "contacting" refers to the bringing together into physical or chemical communication of indicated moieties in an in vitro system or an in vivo system. For example, "contacting" an HBV virus with a compound in the invention may include the administration of a compound in the present invention to an individual or patient, such as a human, having an HBV infection, as well as, for example, introducing a compound of the invention into a sample containing a cellular or purified preparation containing cccDNA.

As used herein, the term "individual" or "patient," used interchangeably, refers to any animal, including mammals, such as mice, rats, other rodents, rabbits, dogs, cats, swine, cattle, sheep, horses, or primates, such as humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder (i.e., including arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., including reversing the pathology and/or symptomatology).

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and the like, avian species, such as chickens, turkeys, songbirds, and the like, i.e., for veterinary medical use.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including the compounds of formulas (I) or (II) may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

Additional information regarding the preparation of the present compounds for administration and the formulation of compositions according to the present invention is provided infra.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, multikilogram or commercial industrial scale.

For compounds herein in which a variable appears more than once, each variable can be a different moiety selected from the Markush group defining the variable. For example, where a structure is described having two R groups that are simultaneously present on the same compound, the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The present invention is further described in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

EXAMPLES

Modulation of HBV cccDNA

DHBV cccDNA in LMH Derived Dstet5 Cells is Efficiently Produced and Transcriptionally Active.

Most HBV producing cells lines produce HBV gene products from an HBV transgene integrated into the host chromosome, and thus cccDNA is not the major source of viral product. This makes screening for drugs that target cccDNA difficult. Cell lines were produced in which viral gene products are dependent upon cccDNA. It was established human Hep G2 and chicken hepatoma (LMH)-stable cell lines for this purpose with tetracycline (tet) regulated HBV/DHBV. As shown in FIG. 1, after culture in the absence of tet and presence of 2 mM of foscarnet (PFA) to block viral reverse transcription, DHBV RNAs accumulate, but DHBV replication is arrested at the stage of pgRNA-containing nucleocapsids (lane 0). Upon addition of tet back to media to block transgene transcription, and removal of PFA to allow the viral DNA synthesis in the pgRNA-containing capsid to proceed, there is a rapid decline of viral RNA (day 1 and 2), with an eventual increase to a higher level when cccDNA is made after day 3.

Figure 2:
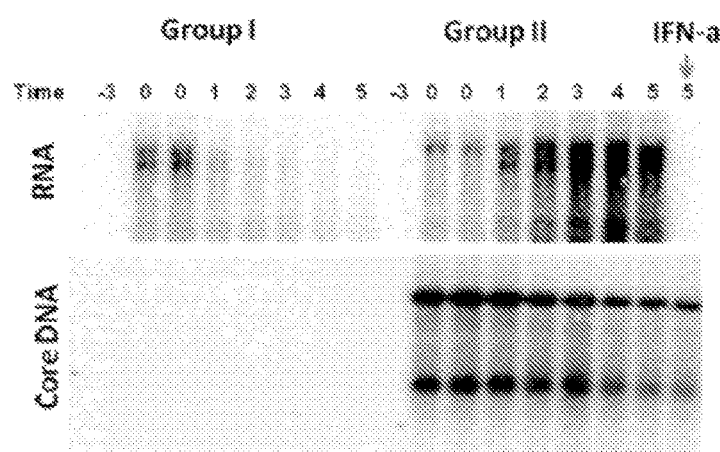
FIG. 2 relates to experiments demonstrating that cccDNA can be inhibited by IFN-a.

These results imply that cccDNA is efficiently formed and transcriptionally functional in dstet5 cells. These results are more thoroughly demonstrated in FIG. 2, where, under the conditions specified in which the transgene transcription is blocked with tet, appearance of new HBV RNA is closely associated with appearance of cccDNA (FIG. 2 Group II, core DNA shown), whereas, viral transcripts are rapidly degraded (½ life~3 hrs) in cells in which both cccDNA synthesis and new transgene transcription is blocked (FIG. 2, Group I)

Identification of Compounds that Potently Repress DHBV cccDNA Transcription.

With a system and conditions under which viral transcripts are produced in a cccDNA dependent manner (FIGS. 1, 2B), approximately 100 compounds were screened, including those from the inventors' in-house small compound library, those present in the inventors' Natural Products collection, and selected compounds including inhibitors of cellular epigenetic modification enzymes, including HDACs, HATs, Sirtuins, histone methyltransferases, histone demethylases and DNA methyltransferases. Numerous compounds, including the four compounds shown in Table 1, significantly reduced the amounts of cccDNA-derived DHBV pgRNA. All possess HDAC class I inhibitory activity.

TABLE 1

Compounds that repress HBV cccDNA function and their activity against HDACs[1]

| Hit | Apicin | Trichostatin A | Suberoyl bis hydroxamic acid (SBHA) | 4-(dimethylamino)-N-[7-(hydroxyamino)-7-oxoheptyl] benzamide (M344) |
|---|---|---|---|---|
| HBV cccDNA ($EC_{50}$, uM) | 0.183 | 0.480 | 2.50 | 6.25 |
| Toxicity ($CC_{50}$, uM)[2] | >20.00 | >20.00 | >40.00 | >100.00 |
| Selectivity Index (SI)[3] | >100 | >40 | >16 | >16 |
| HDAC-I inhibitor? | YES[4,5] | YES[5,6,9] | YES[4,6,7,10] | YES[4,7] |
| HDAC-II inhibitor? | NO[3,7] | YES[4,5,6,9] | YES & HDAC III[11] | YES & HDAC III[7,11] |

[1]Compounds found to suppress HBV cccDNA function in the dstet5 system, described in Prelim Evid., as illustrated in FIG. 2.

[2]Toxicity from our assays on dstet5 cells, as in text; Selectivity Index (SI) is the toxicity $CC_{50}$ divided by the Effectiveness EC50, see text.

[3]Selectivity Index (SI) is concentration that reduces 50% of cell viability ($CC_{50}$) divided by the concentration that reduces 50% of the HBV specific signal (RNA and/or HBeAg) ($EC_{50}$).

[4](7);

[5](15)(26);

[6](45);

[7]Reaction Biology Monograph;

[8](33);

[9](13);

[10](14);

[11](38)

Structures

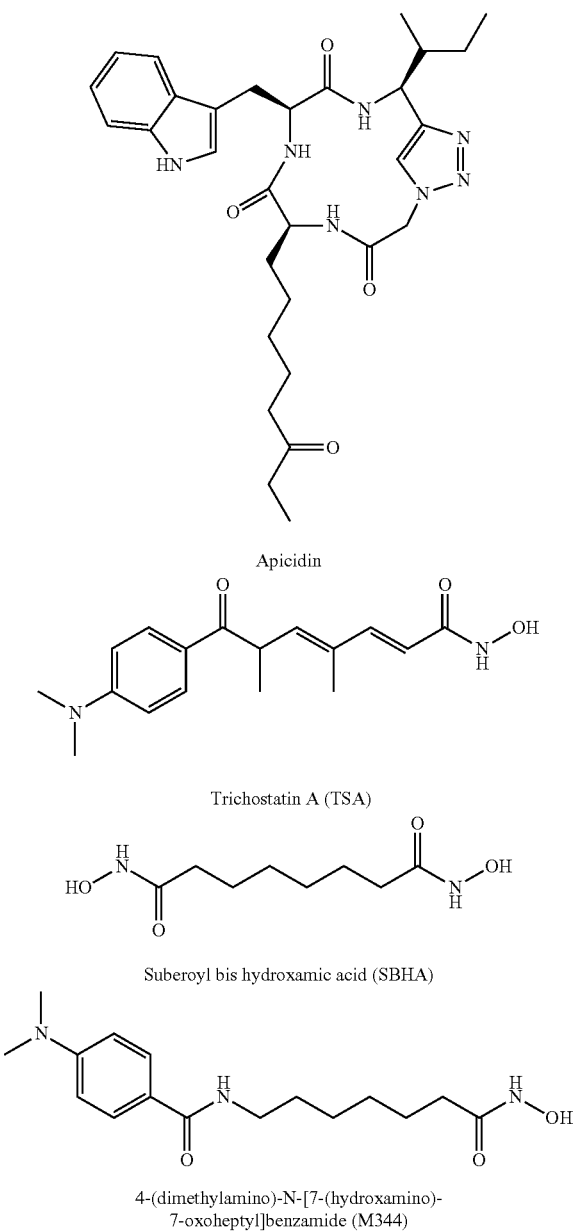

Apicidin

Trichostatin A (TSA)

Suberoyl bis hydroxamic acid (SBHA)

4-(dimethylamino)-N-[7-(hydroxamino)-
7-oxoheptyl]benzamide (M344)

Figure 3:
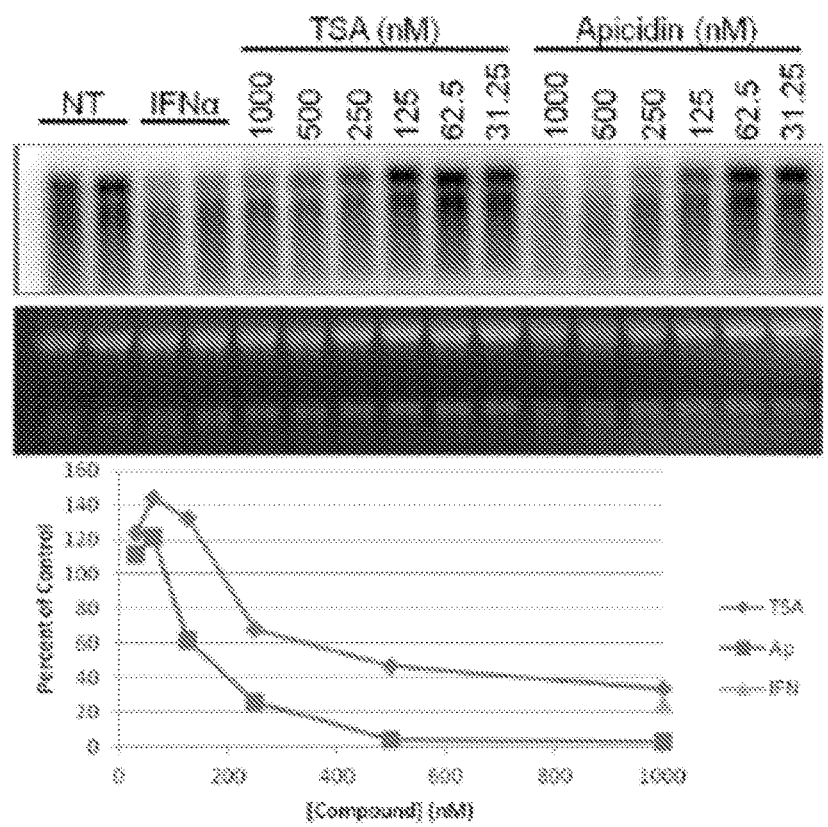
FIG. 3 pertains to the present finding that Apicidin and TSA repress cccDNA transcription.

As shown in FIG. 3, since Apicidin potently inhibited cccDNA (EC50~180 nM), with no toxicity at up to 20 uM for five days, and has nanomolar activity against class I but not class II HDACs, it appears that HDAC II inhibition is not necessary to suppress HBV in this system.

Apicidin and TSA Repress HBV cccDNA Transcription.

Figure 4:
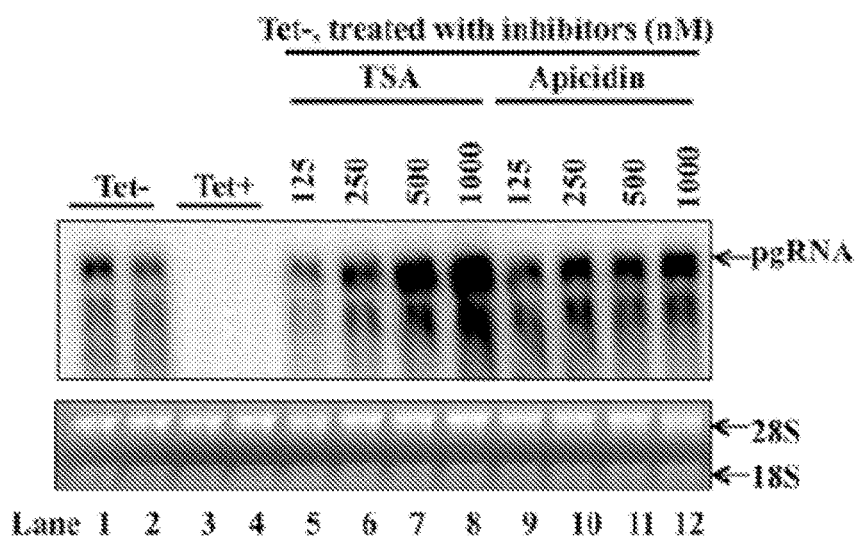
FIG. 4 relates to the discovery that HDAC inhibitors dose-dependently stimulate DHBV pgRNA synthesis from transgene integrated in a host cellular chromosome.

FIG. 3 shows that Apicidin and TSA repress cccDNA transcription in Dstet5 cells. Evidence was also obtained demonstrating that these compounds also repress HBV cccDNA transcription in the HepG2 cells. In marked contrast, it was observed that Apicidin and TSA dose-dependently stimulate DHBV pgRNA transcription from transgene integrated in host cellular chromosome (FIG. 4). This is more typical of cellular gene responses to HDAC inhibitions and suggests that unlike chromosomal DNA, transcription from cccDNA "minichromosomes" are regulated differently. Moreover, there is even evidence that cccDNA levels were reduced, indicating, as seen in the Duck system, that transcriptional repression is followed by destabilization.

Effect of Compounds Upon HBVcccDNA Transcription in Human Hepatoma Cells.

HepDE19 cells are seeded into 6-well plates, cultured in the presence of tetracycline until confluence. Tet is removed from the culture media to allow pgRNA transcription, DNA synthesis and cccDNA formation to occur. Tet is added back to culture media to shut off transgene transcription. After day 3, the cells, in different wells, are left untreated or treated varying concentrations (i.e., 0.1 to 10.0 uM) of each of the "Test" compounds (four "hits" from Table 1 and ~20 analogues) for 2 days. Intracellular HBV cccDNA, viral RNA and core DNA are quantified by Southern/Northern blot hybridization assays as described above and in known procedures. Intracellular full-length HBeAg precursor and secreted HBeAg are quantified with Western blot and ELISA assays respectively. HepG2.2.15 cells are used as a control, because all HBV expression is primarily from the HBV transgene in these cells. Interferon alpha, which has been shown to inhibit cccDNA transcription, and di substituted-sulfonamides (DSS) CCC-0975, which inhibits cccDNA formation (from our screen, Guo 2012) will be included as positive drug controls. In some experiments, cultures are maintained for varying times (days) after removal of "Test" drug from the culture medium, to determine the durability of any drug induced repression of HBV cccDNA. In order to determine the selectivity of the testing compounds on cccDNA transcription, effects of the testing compounds on the expression of a panel of cellular genes, including, but not limited to, alpha1 antitrypsin, albumin, are also measured by quantitative RT-PCR or Northern blot hybridization. The cytotoxicity of the compounds are determined by MTT assay in parallel cultures.

The amount (0-100%) of reduction of HBeAg and HBV transcripts is taken as a measure of HBV cccDNA transcriptional repression. The amount (0-100%) of HBV cccDNA reduction is taken as a measure of destabilization and degradation of HBV cccDNA. The amount (0-100%) of repression of A1AT and/or albumin mRNA reduction is taken as a measure of cellular function inhibition in specificity determination. The amount of MTT (0-100%) activity is taken as a measure of cell viability and the basis of cell cytoxicity (CC). The Selectivity Index (SI) is as in the Table 1 legend.

Effect of Compounds Upon WHV cccDNA Transcription in Primary Woodchuck Hepatocytes.

Woodchuck Hepatitis Virus (WHV) has been a useful model for evaluating therapeutics for HBV. Therefore, it is useful to know, for planning, if the lead compounds are active against WHV. Primary woodchuck hepatocytes cultures (PWHCs) are prepared by plating collagenase treated tissues, derived from small section biopsies obtained from chronically infected woodchucks, under conditions where 50-90% of the hepatocytes harbor WHV, and the cultures (90% or greater) are hepatocytes and can be maintained for at least two months in culture, as done previously (see Fletcher S P, et al. 2012. *Transcriptomic analysis of the woodchuck model of chronic hepatitis B. Hepatology: In press*). Within 7 days of seeding, cultures are incubated in the absence or presence of test compounds, and the amount of WHV gene product in the culture medium (WHV virion associated DNA; WHs) and intracellularly (WHV DNA, WHV RNA transcripts) are determined, using the similar methods as previously used and published (Guo, H., et al.

2010. Production and function of the cytoplasmic deproteinized relaxed circular DNA of hepadnaviruses. *J Virol* 84:387-396; Guo, et al. 2011. *Alkylated porphyrins have broad antiviral activity against hepadnaviruses, flaviviruses, filoviruses, and arenaviruses. Antimicrob Agents Chemother* 55:478-486)

Where WHV is sensitive (as suspected) to Apicidin and other candidate cccDNA inhibitors, at SI's similar to that in the avian and human systems, then chronically infected woodchucks are used for an in vivo proof of efficacy study.

The inhibitors are ranked (i) by their selectivity index (SI), with the most selective in inhibiting HBV cccDNA transcription versus cellular viability, and then cellular function, being the most attractive; (ii) by their potency of inhibiting cccDNA transcription (lowest EC50) and finally, (iii) by "critical chemistry" (scalability type/formulation) issues. The compounds with the lowest values of $EC_{50}$ (concentration that inhibits 50% of the cccDNA-transcribed RNA) and greatest SIs, are the most attractive.

Identification of HDAC Isoform

Each of the compounds identified in the primary screen share the property of having HDAC inhibitory activity (see, e.g., Table 1). It is likely that HDAC inhibition is either part of, or central to, the mechanism of the HBV antiviral action of these compounds. Although it is not necessary to precisely know the compound's mechanism, this information would be helpful in selecting or designing modified compounds, as well as in forecasting and reducing possible in vivo toxicities, and designing clinical studies. Also, since crystal structures are available for many HDACs, future drug design can be assisted. Taken together, the growing experience with HDAC inhibitors in research and in people, can could provide direction for the present clinical designs and future plans.

HDACs deacetylate polypeptides (i.e., histones) and are classified into four categories, based on function and DNA sequence homology. Class I and II HDACs are inhibited by trichostatin A (TSA). Apicidin efficiently inhibits class I, but not class II HDACs. Class III HDACs, called sirtuins, are a family of NAD+-dependent proteins, not affected by TSA. Class IV is considered an atypical category, based on DNA sequence. Because Apicidin and TSA potently inhibited cccDNA transcription, HDAC isozymes in classes I and II are most relevant. However, since Apicidin inhibits only Class I, the initial focus is only on this class.

Experimental details: Silencing of HDAC isozyme transcripts with shRNA and the effect upon HBV cccDNA function. Short hairpin RNAs (shRNAs) expressed from lentivirus transduction vectors are now standard tools to repress translation of the transcripts to which the shRNA is homologous. A focus is placed on the class I HDAC isozymes. Therefore, confluent monolayers of HepDE19 cells expressing HBV gene products in a cccDNA dependent manner (as described supra, after tet repression) are transduced with 100 ul of lentivirus (~5×10$^7$/ml) in transduction mixture, expressing shRNA selective for class I-1, 2, 3 or 8 isozymes under conditions where at least 95% of the cells receive and express the shRNA. This is determined by expression of reporter from the retroviral transgene. The shRNA lentiviral expression vectors are provided by the vendor as transduction ready, and each vector targets different HDACs of sub-class I. They are purchased from vendors (e.g., Santa Cruz Bio, OpenBio), and contain and express short hairpins with 19-25 nts homologous to each HDAC isozyme transcript to be targeted. For example, one HDAC 1 specific shRNA contains 5'-GAT CCC CGC AGA (SEQ ID NO:1) . . . ATC TGC TTT TTG GAA A (SEQ ID NO:2)-3', and others are similarly designed but specific for the other shRNAs, as provided by vendor and from previous work. There is 4- and 5-fold coverage for each HDAC isozyme. Control vectors contain scrambled sequences, and are used as negative controls. After 5 days of shRNA lentiviral transduction, repression of the specific HDAC is quantified by RNA analysis and western blot (with HDAC specific probes and monoclonal antibodies provided by vendor), and the amount of HBV cccDNA and cccDNA dependent transcript, and HBeAg, is measured as was performed in preceding description. Where transient transduction approaches are unsatisfactory, although a bit more involved, stable transductions are used, since shRNA constructs, with selectable markers are used. The amount of cellular gene expression (A1AT and albumin mRNA) are also quantified, as described above, as a specificity control. Positive controls include incubation of the HepDE19 cells with Apicidin at 1000 nM, a concentration which represses HBV cccDNA (and will have been validated on HepDE19). Each of the different HDACs has been associated with specific cellular functions (i.e. 1, up regulation of p53, 2 & 3 p21, 8, deacetylation of H4) which are quantified as evidence of successful HDAC sub class inhibition, should that be desired.

Given the potency of Apicidin, it is expected that silencing at least one of the Class I HDACs will result in significant repression of HBV cccDNA function. It is recognized that the HDAC inhibitors, which act on multiple HDACs, may have a greater effect than can be achieved by a single HDAC transcript knock down. However, we knock down experiments are also performed using lentivirus combinations covering all class I enzymes, since this should repress HBV cccDNA if class I enzymes are involved (as Apicidin suggests), but multiple enzymes must be repressed to detect the HBV cccDNA inhibition.

Where silencing a specific or group of HDAC transcripts results in repression of HBV cccDNA function, this is validated as a target for HBV antiviral action, and corroborated the finding that a mechanism of anti-HBV cccDNA action of the identified compounds involves HDAC inhibition. The compounds could, of course, use other mechanisms for HBV cccDNA suppression, but it will at least be known that HDAC inhibition does repress HBV cccDNA, and the door is now open for this new class of HBV therapeutic strategies.

Determining which of the Identified Compounds have the Greatest Inhibitory Effect Upon the HDACs Isozymes Responsible for HBV cccDNA Repression.

Having identified specific HDAC isozymes that are responsible for regulating HBV cccDNA, it is useful to identify the compounds that have the greatest selectivity for inhibiting the HBV cccDNA regulating isozyme. This allows for advancing the compounds with the greatest selectivity and help avoid off target effects resulting from needlessly inhibiting HDAC isozymes that are not involved in regulating HBV cccDNA. We note that of the four compounds denoted above in Table 1, Apicidin has the greatest selectivity index, and is also the one with the narrowest HDAC inhibitory profile (selective for HDAC class I). Therefore, it is possible to achieve even greater selectivity by avoiding broad HDAC inhibitors and zooming in on the specific HDAC sub-isozyme that is sufficient to repress HBV cccDNA.

Enzyme assays for each of the HDAC class I (1,2,3,8) isozymes are available as commercial kits, with positive and negative competitive inhibitor controls. Kits are purchased corresponding to the relevant isozyme as identified above, from BioTeK, BPS Bioscience, or other available sources. Briefly, with the BioTek system, sub class specific purified HDAC enzyme (recombinant, at ~10-50 ng/vessel) is provided, with a fluorogenic substrate, detected following deacetylation, with developer in a premixed reaction. The enzymes that were shown by silencing to be involved in HBV cccDNA repression are purchased. Varying amounts of control or each of the experimental compounds are incubated with the enzyme reaction mix The assay read-out is optimized for linearity both as a function of time and enzyme concentration. Kits from the concentrations of the testing compounds required to inhibit 50% of the deacetylase activity of an HDAC isoform (i.e. IC50) are calculated by regression analysis using SigmaPlot software (Systat Software, Inc., San Jose, Calif.).

Ideally, and most logically, compounds found to be active according to the procedures described above are active against HDACs found to be most involved in HBV cccDNA regulation, and these represent the favored compounds. Compounds that are active but broadly inhibit HDACs, some of which are found to be irrelevant to HBV cccDNA regulation, are somewhat less favored, since they may bring unnecessary side effects. Where, on the other hand, there is a disconnect, and the compounds active in the preceding assays do not inhibit the HDACs found to be most important to HBV cccDNA regulation, the compounds are advanced based on HBV cccDNA suppressive activity, and not HDAC inhibitory ranking.

Evaluation of Lead Compounds for their In Vitro Absorption, Distribution, Metabolism and Toxicity (ADMET) Properties HBV Producing Cells and Non Producing Cells Introduction and Rationale In vivo experiments are expensive and ethically constrained. Before testing in animals, it is therefore prudent to initially profile compounds for potential toxicity and other cell-serum—interactive properties that are, to the extent possible, predictive of in vivo performance. These studies have become standards in the field. Toxicity in replicating cells has also been found to be a good way to rank compounds with respect to toxicity. Finally, differing formulations are also usually necessary, before moving on to in vivo work, because solvents used in the tissue culture setting are not always compatible with in vivo administration. These are used, as below. An innovation in in vitro "ADMET" is presently proposed, in which the profiling is carried out with HBV producing cells in the presence of a currently approved antiviral therapies, in addition to the routine ADMET.

It is likely that new anti-HBV drugs, will be used in combination with the other HBV antiviral drugs, in current use. Combination therapy is standard for HIV and HCV and other infectious diseases. It is important to know if a new drug to treat HBV has toxicities or other altered profiles in the presence of the current standards of care, since there is evidence that many otherwise well tolerated medications have selective toxicities in chronically infected individuals. HBV producing cells may be more sensitive to some emdications than are non producing cells (Block, in progress). Therefore, the toxicity experiments, below, are carried out in the absence as well as the presence of HBV polymerase inhibitors and, in some cases, interferon alpha (IFNa).

Some of the present lead compounds may have already been used in animals (by others), there may be considerable information available. On the other hand, some of the leads may be new compounds for which there is no animal data. Compound profiles are also examined in the context of HBV infection, for the reason stated above.

Finally, compounds that suppress wild type HBV cccDNA function and are well tolerated in vitro are tested for their ability to suppress cccDNA from HBV that is resistant to HBV polymerase inhibitors. Depending on the results of the preceding studies, human and/or duck HBV transfection (and for the duck, infection) systems are used.

For every experiment described below, controls with known toxicity, metabolism, protein permeability, membrane transport and defined formulation properties are included. For example, Barraclude and FIAU are included as controls for compounds that have no detectable toxicity in HBV producing cells, and those that do, respectively, and have reported PK and TK properties for which comparisons can be made.

Experimental Detail: In Vitro "Administration, Distribution, Metabolism, "Elimination" and Toxicity" (ADMET) Studies.

Some of these experiments are carried out under contract by a Vendor (i.e. Absorption Systems) and others, particularly where HBV producing cells and material are used, are carried out by the present inventors, as indicated, below.

Standard Cytoxicity Assays.

Human hepatoma (HepG2, Huh7, HepRG) and HepG2-derived cell lines supporting constitutive (HepG2.2.15) and tetracycline-inducible HBV replication (HepDE19 and HepDES19) are seeded into 96-well plates at a density of $2 \times 10^4$ cells per well. Cells are treated with a serial dilution of testing compounds. The culture media is changed every other day. MTT assays are performed at day 2, 4, 6, 8 and 10 day since treatment.

Toxicity to Multiplying Cells:

Varying concentrations of lead compound(s) are incubated with HepRG cells seeded at low density (100 cells per well of 32 mm dish) under HBV producing and non producing conditions, and cultured for 10 days, with media changes every 3 days.

Metabolic Stability in Human and Mouse Liver Microsomes:

The compounds are incubated with human and mouse liver microsomes from HBV producing and non producing cells (tissue culture source as above) in the presence of NADPH. In addition, the stability of compounds are evaluated in the presence of human simulated gastric fluid and simulated intestinal fluid. The purpose of this set of experiments is also to determine if the compounds are metabolized by the digestive enzymes. Since orally available compounds are pursued, it is important to find out what metabolites, if any, might be produced in the GI tract.

The toxicity and metabolic stability studies are carried out in the absence and presence of concentrations of lamivudine, barraclude, telbivudine, tenofovir and/or adefovir that are equal to and multiples (~0.1 ug/ml, for barraclude, ~10 ug/ml for lamivudine) or interferon alpha (IFNa) of the serum levels typically achieved in people. The cccDNA suppressive test compounds are used at 10 times their IC50, as determined in assays described above. Control compounds (with established toxicities and established metabolic profiles) are also included with each panel of tests (i.e. FIAU, statins, etc).

Plasma Protein Binding:

Equilibrium dialysis is used in this assay to determine the percentage of compound that binds to human plasma proteins (by Vendor).

Bidirectional Permeability:

This assay is used to determine the permeability of compounds through Caco-2 cell monolayers in the apical-to-basolateral and basolateral-to-apical direction. (Contractor)

Antiviral Activity of Lead Compounds in the Presence of Interferons (IFNs).

The experiments above explore the in vitro ADMET of the lead compounds when used in combination with polymerase inhibitors or interferons in uninfected cells. It is also important to determine if the lead compounds have an impact upon an established antiviral agent's antiviral properties. Compared with pol inhibitors, IFN alpha (a) is less frequently used to manage HBV. When used, it is only for a period of months, unlike pol inhibitors, which are used for years and more likely to be co-administered with a cccDNA inhibitor. However, given the fact that IFNa mechanisms of antiviral action and toxicities may involve HDACs, it does make sense to evaluate the presently disclosed cccDNA inhibitors for their interaction profiles with IFNa, to the extent this can be evaluated in vitro. Therefore, the dSTET cells and AD38 cells programmed to produce transcripts from HBV cccDNA (as in prelim evidence and Cai 2012) seeded at cloning densities (for growth studies) and semi confluence (for antiviral/cccDNA transcription studies) are incubated in the absence and presence of varying concentrations of candidate cccDNA inhibitor and the absence and presence of amounts of either avian IFN or human IFNa known to suppress HBV in vitro. Cell viability and the amount of HBV cccDNA derived gene products (transcripts) produced are determined as in previously described procedures and those known in the literature.

The compounds are also tested for in vitro activity in the presence of the currently used polymerase inhibitors. The emergence of mutant viruses resistant to the nucleoside/tide inhibitors of the HBV polymerase is a problem in the management of chronic infection, although the problem varies with the polymerase inhibitor used. Thus, compounds that suppress wild type HBV cccDNA function are tested for their ability to suppress cccDNA from HBV that is resistant to HBV polymerase inhibitors. All of the mutant viruses (DHBV and WHV) needed are available. Human and/or Duck HBV transfection (and for the Duck, infection) systems are used. Given the distinct mechanism of action, the present compounds retain antiviral activity.

Formulation Optimization:

For selected compounds, dosing vehicle development suitable for oral gavage are evaluated. The test vehicles include 1) pH manipulation, 2) co-solvents (such as glycin, polyethylene glycol propylene glycol, ethanol etc), 3) surfactants (such as polysorbates, polozamer, polyoxyl castor oil, glyceryl and PEG esters), 4) Non-aqueous systems (such as sesame oil, medium chain triglycerides, soybean oil, oleic acid), 5) complexing agents (such as cyclodextrins).

From an ADMET perspective, preferred are compounds that have properties similar to Barraclude, with respect to tolerability. Also preferred are compounds that have the same toxicity and metabolic stability profiles in the absence of HBV polymerase inhibitors (lamivudine, barraclude, interferon etc) as in their presence. Compounds with selective toxicity to HBV producing cells are disfavored, disqualified, or advanced with extra caution. Compounds that have enhanced, or enhance, the toxicity of current HBV antivirals, or antagonize the antiviral, activity those compounds, are still advanced, but with caution and tested in in vivo experiments for the possibility of enhanced toxicity in combination. It is possible to propose that the cccDNA active compounds not be used (or only used cautiously) in combination.

Lead Compounds with Favorable In Vitro Properties are Scaled Up and Tested for In Vivo Toxicity, Pharmaco Kinetics (PK) and Efficacy Pharmacokinetic, Toxico-Kinetic (TK), and Dose Range Finding Studies.

Prior to conducting in vivo efficacy studies, which are expensive, ethically constrained, and consume great amounts of compound, it is necessary to determine the maximum tolerated doses (MTDs) and pharmacokinetic properties (PK) of the candidate drugs, in vivo, in uninfected animals. This permits the identification of compounds worthy of advancement and establish proper dosing and routes of administration. Compounds are tested for efficacy in either (or both) duck and/or woodchuck models of chronic hepadnavirus infection, since these are the established and predictive animal models. The rationale for duck versus woodchuck is described below. Regarding Apicidin itself, a great deal will already be known about its PK/TK in animals, since it has already been used in mice. However, even for Apicidin, and certainly for any other of the present compounds, new PK, TK for the Duck and woodchuck study are needed. Therefore, a series of murine and rat PK and TK studies are conducted as follows.

Experimental Detail—Single Dose Pharmacokinetic Study in Mice, Ducks and, if Indicated, Woodchucks.

The objective of this study is to obtain volume of distribution, systemic clearance, half-life (T½), maximal plasma concentration (Cmax) and bioavailability. These parameters are used to evaluate the clearance and bioavailability of each imino sugars so that the compounds can be ranked by their ability to maintain plasma concentration. In general, greater than 50% bioavailability is preferred for compounds to be advanced.

As described above, candidates are administered via i.v. injection (5 mg/kg) or given orally (25 mg/kg) to mice (6 week old Balb/c; 6 mice/group); Peking Ducks (6 week old) or woodchucks (3 per group). Clinical observations are recorded at several intervals after dosing. Blood and urine samples for pharmacokinetics are collected predose, and at 5, 15, and 30 min, 1, 2, 4, 6, 8, 16 and 24 h post-dose. Samples are analyzed for the presence and amounts of administered drug (drug or prodrug) and in the case of administered prodrug, for the presence and amount of "drug" metabolite" as well. The samples are analyzed by Absorption Systems, who has established mouse plasma assays for our other compounds.

Tissue distribution (murine).

Tissue is taken from mice (3 per dose group) receiving a single oral or iv administration of compound at various times after administration. Knowledge of the tissue distribution of a compound can significantly aid in evaluating potential as successful drug candidate. Although other in vitro parameters, such as plasma protein binding and volume of distribution have prediction values for rate and extent of distribution to extravascular tissues, the liver tissue concentration of drug is probably most relevant to efficacy. A focus is maintained on liver, in comparison to serum, kidney and abdominal fat tissue/lymph nodes, for tissue concentration of candidates, using endpoint samples, following the single administration of the compound by an i.p. and oral route in mice. One point of interest is if active compound builds up in key tissue, which provides insights regarding its effective half life, in tissue. That is, although the serum half life of a drug might be ~2 hours, it could have a tissue half life in liver several fold times that, explaining a greater than expected efficacy (for a given dosing regimen), or greater than expected toxicity.

Dose-Finding Maximum Tolerated Dose (MTD) Study.

Since the compounds are evaluated for antiviral activity in murine models, it is important to know the tolerability of the compounds in mice. Balb/c mice (6 week old, 6 per group); Ducks (6 week old, 3 per group) will be dosed by oral gavage (since we are pursuing orally available compounds) either "vehicle" alone, or vehicle in which compound has been dissolved. From previous experience, the range of compound administered is likely between 100 mg/kg to 500 mg/kg, 5 mice per dose group. Animals will be observed for up to 14 days, with daily readings of weight and an endpoint of survivability. Routine histology and clinical chemistry studies are be performed. The highest dose of compound that does not result in any mortality/toxicity is considered to be the MTD. Woodchucks can not be used for this MTD study; extrapolations from the murine study, combined with the PK woodchuck study will be necessary.

The compounds are ranked for their oral bioavialibility, tolerability, and half lives. The ideal compound is able to reach and sustain serum or liver tissue levels at least 10 times the tissue culture IC50 concentration, with soluble, oral, single day dosing, and have MTDs more than 100 times that of the tissue culture IC50. Compounds are ranked with respect to these qualities, and the best and second best will be advanced.

Is the Lead Compound Efficacious in Chronically Infected Animal Models, In Vivo?

Having demonstrated in vitro efficacy, and determined safe and rationale dosing for in vivo work, it is be important to know if the lead compounds can control viral levels in validated animal models of chronic HBV. This represents the first time a small molecule drug that targets cccDNA will have been tested in animals. Outcomes consistent with a safe, selective and cccDNA targeting agent are of interest. Efficacy end points include: rapid and coordinated reduction in viremia, antigenemia as well as amount of intra-liver cccDNA and replicative forms which would be indicative of cccDNA suppression. These goals dictate the animal models that are used, and length of treatment that is studied.

Several animal models of chronic HBV infection exist, and each has virtues as well as disadvantages. Ducks and woodchucks can be experimentally chronically infected with duck and woodchuck hepadnavirus, respectively. There are now several murine models, but since transgenic mice bearing HBV transgenes do not produce HBV from cccDNA templates, to test a cccDNA targeting compound, a chrimeric mouse with human hepatocytes would be necessary, such as the uPA mice. Practical considerations require making a choice. Experiments are designed for evaluation in the Duck model of chronic HBV, since the compounds are active against the Duck virus in avian cells in culture are already known. Studies in the chronically infected woodchuck are also prepared, since this is an established model for testing HBV therapeutics and is a natural infection. The uPA mice are very expensive but will are if woodchucks are not sensitive to the drugs, but human HBV is.

Therefore, preferred compounds are scaled up to the amount necessary and tested for efficacy, as defined below, in the following Duck, and if appropriate, woodchucks.

Experimental Detail—Scale Up Production of Preferred Compounds.

Apicidins are produced in fermentations by *Fusarium* (i.e. sp. ATCC 74322). The strain is inoculated into a nutrient medium called MED5, shaken at 220 rpm, for 12-16 days in a controlled humidity atmosphere. At harvest, whole broth is extracted with methylethylketone and the extract is fractionated by gel filtration on Sephadex followed by final purification by RP-HPLC. Yields are on the order of 250 mg/L so scale up to gram amounts are routine.

Duck Hepadnavirus Efficacy Study.

Since it is known that Apicidin is highly active against the DHBV, in culture, it is tested in a chronically infected duck. The goal of this study is to determine the antiviral potential of preferred compounds. Serology and histology are secondary.

Six-week-old Peking Ducks, chronically infected with DHBV type 16 (Alberta Strain), are used. At 6 weeks, viremia and liver mass in ducks tends to have stabilized. Ducks are given, by either i.m. or oral gavage (depending on Aim 4 PK/TK results), test compound (3 dose groups, with dosing amount and frequency to depend on PK results, but aiming to achieve stable serum levels of at least 10 times the tissue culture IC50). There are three dose groups with 5-6 animals per dose group. Control dose groups (6 animals each group) include placebo treated animals and animals treated with either barraclude (1 mg/kg) or lamivudine (40 mg/kg) per day. At least three animals from all dose groups contribute at least one pre treatment and one post treatment liver biopsy. Treatment is for 10 weeks, since this exceeds the time for lamivudine to suppress viremia to beneath detectable levels and the reported ½ life of cccDNA in the duck. Ducks are followed with weekly serum collections for an additional 4 weeks after withdrawal of drug. Serum will be collected weekly.

Weekly serum is tested for standard "lab values" (hematology, albumin, AST, ALTs, The amount of DHBV viral DNA, sAg, sAb in the circulation is determined. Liver tissue derived from biopsies (some pre treatment and end of treatment from the same animals) is examined for DHBV DNA (cccDNA, replicative forms) and DHBV core (immunostained).

WHV-Infected Woodchuck Study.

The study uses 10 groups, with 5 animals per group, with drug treatment for 10 weeks followed by 10 weeks off drug (to test durability of affect). Due to variability in the levels of viremia and antigenemia, animals are stratified to groups by WHV viremia and antigenemia levels as determined seven days prior to study start, so that the average levels of both viral markers are evenly distributed among all groups of animals. Animals with abnormally low WHVsAg levels are not used in this study. Compound is administered daily, by a route and frequency to be finalized after bioavailability studies in rodents. The first day of dosing on the study is Study Day 1. Study Day 1 dose levels are calculated on a pretest body weight, and body weights are taken weekly for dose administration. Dosing range is as for the mouse study over four doses, with Group 10 treated with Barraclude as a reference compound (Tennant).

The primary endpoint is a dose dependent reduction in viremia and antigenemia on and off drug achieving durable off drug reductions.

Viability and Animal Health.

Clinical observations are performed and recorded once daily for morbidity and mortality. Further toxicology is addressed via hematology, serum chemistry, and histology examination. It is also important to consider all biochemical and immunological endpoints in the context of general animal health to insure that decreases in viremia or antigenemia or other putative beneficial outcomes are not a secondary consequence protocol (compound) toxicity. Gross physical characteristics (weight, stool and urine output and characterization, are determined on a weekly basis. In addition, liver function tests (performed on samples collected monthly), hematology and chemistry (performed on pre, mid and end of treatment samples (as described in the table) and, for selected animals (at pre-dose, mid dose and end of treatment times), histology on punch biopsy derived liver sections are also performed for assessment of toxicity as well as efficacy Liver function test are determined by commercial service in the monthly samples as a marker of liver viability Evidence of Humoral Responsiveness.

The presence of antibodies that recognize WHsAg are determined by an ELISA. This assay is such that even WHs Abs complexed with antigen are detected.

Toxicology.

Careful toxicology is carried out via hematology and serum chemistry as described for the mouse studies. In addition, histological examination of the punch biopsies of the livers is undertaken, including inflammation, bile duct proliferation, and portal and lobular hepatitis.

WHV Virus Levels in the Serum.

An assessment is performed on weekly (as slot blot hybridization and PCR or bi-monthly (southern blot).

Biopsies.

Liver biopsies are collected before the start, middle, end of treatment, and end of study and used for histology and intracellular WHV DNA examination. Levels of replicative form and intrahepatic covalently-closed circular WHV DNA (WHV cccDNA) are quantitatively determined based on Hirt extraction. For immunostaining, separate tissue is used and accumulation of core and WHsAg in treated versus untreated animals will be determined.

For both the Duck and woodchuck studies, no technical difficulties are expected, since these studies are fairly routine, with all methods and reagents needed for evaluation being in hand. One possible problem with Ducks is the variations in viremia/antigenemia that occur without drug. This is mitigated by using Ducks after 6 weeks of age, in which virology as usually stabilized.

The benchmark of positive activity is LFMAU treated animals. These animals are expected to have uniformly lost HBV viremia and even antigenemia, by 3 and 10 weeks of treatment, in the Duck and Woodchuck, respectively, with numbers of HBV infected hepatocytes greatly reduced, relative to pretreatment and untreated groups.

Inhibition of cccDNA transcription (and stability) should reduce the intracellular and extracellular amounts of all viral gene products (at a rate influenced by their serum half lives), even before there are reductions in the numbers of HBV infected cells (and possibly, out of proportion to the number of HBV infected cell loss). Realistically, the clearest evidence of efficacy of our new compounds is time and dose dependent statically significant reductions in HBV DNA viremia and sAg antigenemia. Given the efficacy of the present compounds, in vitro, an at least a ten-fold reduction of serum surface antigen in either or both models is expected.

DHBsAgWHsAb levels are also measured. Control, chronically infected animals are expected to have no detectable (or very little detectable) Ag. There is a growing body of evidence that chronically infected people (and woodchucks) are capable, and do make, sAb, but it is suppressed or bound with circulating sAg. It is therefore possible that if and as Ag declines, sAb will declare itself.

Biopsy analysis is performed on immunostained for HBV core, sAg, using mounted liver tissue, and with extracts to examine the amounts of HBV nucleic acid, before and after treatment. Ideally, the numbers of infected cells will decline as a function of drug treatment. Useful information includes whether this occurs in a setting of increased hepatitis (cell infiltration).

Serum from animals for 10 & 4 weeks (Woodchuck and Duck, respectively) is also evaluated after drug treatment has been stopped. Stable, off drug, repression of antigenemia, viremia, with appearance of sAbs is considered the obtaining all major objectives. On drug suppression of viremia and antigenemia by amounts exceeding placebo, in the absence of any adverse reactions or events, is considered proof of a drug specific affect.

The animal studies outlined above permit definitive conclusions as to whether the compounds are effective at reducing antigenemia in an in vivo context.

Where inhibition of an HDAC is determined to repress HBV cccDNA transcription, the results are as surprising as they are useful, since HDAC inhibition has generally been associated with gene activation, including HBV DNA integrated into host chromosomes. The results may represent an example of how different is the regulation of HBV cccDNA from most cellular genes and, even if the inhibitors identified herein are not ultimately used in human systems, it is demonstrated that it is possible to non-catalytically inhibit cccDNA with small, pharmacologically, active compounds.

Taken together, this work delivers two very critical answers. First, it indicates the selective suppression of HBV cccDNA function in human and woodchuck cultures. Second, it determines which HDAC (the target of Apicidin) regulate HBV cccDNA. We understand that HDAC inhibition in HBV infected people must proceed with caution, and this work represents direction regarding how to go proceed with a revolutionary new therapeutic strategy.

General Synthesis

The compounds of this invention can be prepared from readily available starting materials using the following general methods and procedures. It will be appreciated that where typical or suitable process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C NMR), infrared spectroscopy (IR), spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in P. G. M. Wuts and T. Greene, *Greene's Protective Groups in Organic Synthesis*, 4th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. The compounds of the invention can be prepared, for example, using the reaction pathways and techniques as described below.

Compound Synthesis

Apicidins have been derivitized and recent analogs 1 and 2

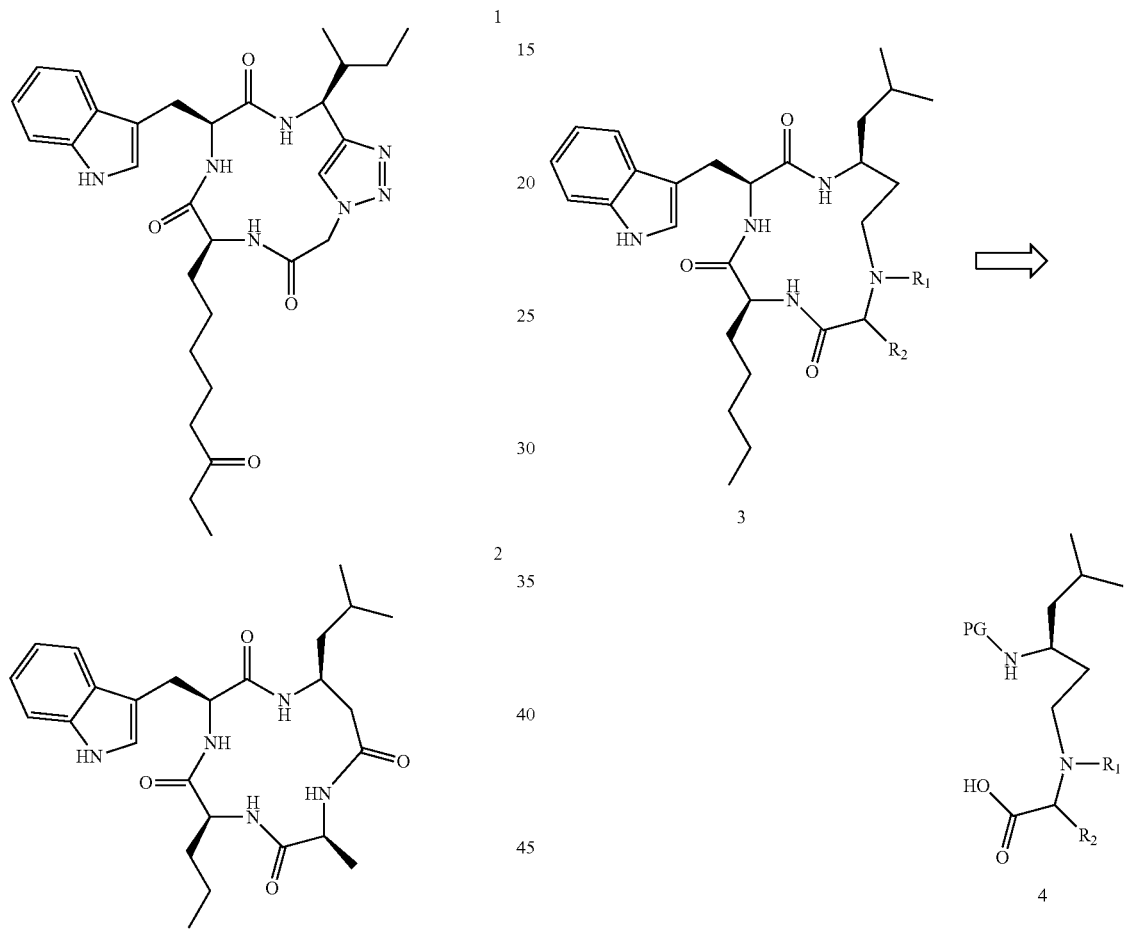

(see Horne, W. S., C. A. Olsen, J. M. Beierle, A. Montero, and M. R. Ghadiri. 2009. *Probing the bioactive conformation of an archetypal natural product HDAC inhibitor with conformationally homogeneous triazole-modified cyclic tetrapeptides. Angew Chem Int Ed Engl* 48:4718-4724; Vickers, C. J., C. A. Olsen, L. J. Leman, and M. R. Ghadiri. 2012. *Discovery of HDAC Inhibitors That Lack an Active Site Zn2+-Binding Functional Group. ACS Medicinal Chemistry Letters*) demonstrate that the Apicidin structure can be modified without loss of anti HDAC potency.

Further analogs were prepared with a focus on improving pharmaceutical properties relative to Apicidin, which has very poor aqueous solubility, oral bioavailability, and half life in vivo. Apicidin derivatives were prepared, inter alia, by standard solid and solution phase methods. In certain embodiments, the reduced beta-isoleucine amino acid derived fragments 4 were prepared in a suitably protected form (PG=suitable protecting group, such as Fmoc or Boc) by solution phase methods and introduced into the amino acid sequence by solution or solid phase means, followed by cyclization using established methods.

---

What is claimed:

1. A compound of formula II:

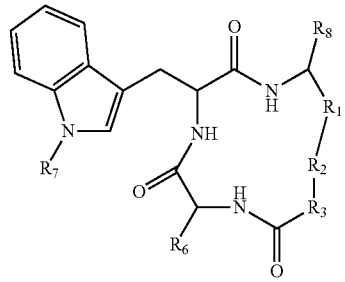

(II)

wherein $R_1$ is $(CH_2)_n$— or —C(=O)—;

$R_2$ is —C(=O)— or —C(Z)N($R_4$)—;

$R_4$ is hydrogen, alkyl, aryl, aralkyl, dialkylaminoalkyl, or carboxyalkyl;

$R_3$ is —CH($R_5$)—;

$R_5$ is hydrogen, —CH$_3$, or an alpha amino acid R group;

$R_6$ is —(CH$_2$)$_m$C(X)Y, —(CH$_2$)$_2$CH$_3$, or —(CH$_2$)$_q$-phenyl-(CH$_2$)$_m$C(=O)NHOH;

X is =O, H$_2$, =N—NH$_2$, or =N—NH—C(=O)NH$_2$;

Y is NHOH or —CH$_2$CH$_3$;

Z is H$_2$ or O;

$R_7$ is hydrogen or alkoxy;

$R_8$ is alkyl or carboxyalkyl;

n is 0-2;

m is 0-6; and, q is 0-3;

or a stereoisomer or pharmaceutically acceptable salt thereof.

2. The compound of claim 1, which is

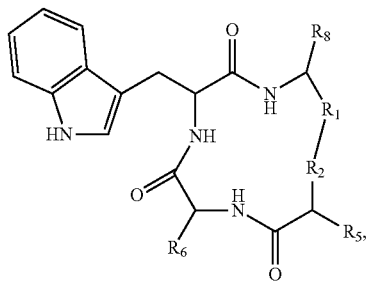

wherein $R_1$ is —(CH$_2$)—, and $R_2$ is —C(Z)N($R_4$)—.

3. The compound of claim 1, which is

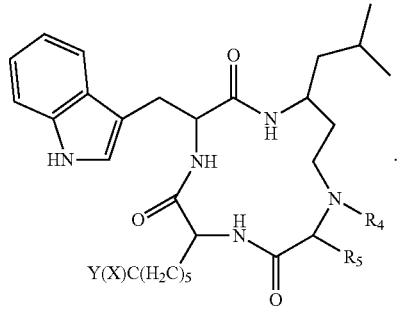

4. A pharmaceutical composition comprising at least one compound of claim 1 and at least one pharmaceutically acceptable carrier, diluent, or excipient.

5. The pharmaceutical composition of claim 4, further comprising an additional anti-hepatitis B infection agent.

* * * * *